(12) United States Patent
Jimenez et al.

(10) Patent No.: US 11,612,496 B2
(45) Date of Patent: *Mar. 28, 2023

(54) MEDICAL DEVICE EMPLOYING A COAXIAL SCREW GEAR SLEEVE MECHANISM

(71) Applicant: SpineX Tec LLC, Gering, NE (US)

(72) Inventors: Omar F. Jimenez, Gering, NE (US); Nicholas R. Powley, St. Paul, MN (US); Andrew G. Fischer, St. Paul, MN (US); Yefim I. Safris, Golden Valley, MN (US)

(73) Assignee: SpineX Tec LLC, Gering, NE (US)

( * ) Notice: Subject to any disclaimer, the term of this patent is extended or adjusted under 35 U.S.C. 154(b) by 636 days.

This patent is subject to a terminal disclaimer.

(21) Appl. No.: 16/529,897

(22) Filed: Aug. 2, 2019

(65) Prior Publication Data

US 2020/0030116 A1 Jan. 30, 2020

Related U.S. Application Data

(63) Continuation of application No. 15/332,066, filed on Oct. 24, 2016, now Pat. No. 10,369,008, which is a
(Continued)

(51) Int. Cl.
*A61F 2/44* (2006.01)
*F16H 25/20* (2006.01)
(Continued)

(52) U.S. Cl.
CPC ........ *A61F 2/4465* (2013.01); *A61B 17/7065* (2013.01); *A61F 2/447* (2013.01);
(Continued)

(58) Field of Classification Search
CPC ...... A61F 2/4465; A61F 2/4455; A61F 2/447; A61F 2/441
See application file for complete search history.

(56) References Cited

U.S. PATENT DOCUMENTS

| 283,218 A | 8/1883 | Rycke |
| 703,251 A | 6/1902 | Haire |

(Continued)

FOREIGN PATENT DOCUMENTS

| EP | 1342456 B1 | 7/2005 |
| EP | 1552797 A2 | 7/2005 |

(Continued)

OTHER PUBLICATIONS

Indian Examination Report for Indian Application No. 952/DELNP/2012 dated Sep. 27, 2018.
(Continued)

*Primary Examiner* — Ellen C Hammond
(74) *Attorney, Agent, or Firm* — Lerner, David, Littenberg, Krumholz & Mentlik, LLP

(57) ABSTRACT

Medical devices in accordance with various embodiments of the present invention employ one or more coaxial screw gear sleeve mechanisms. In various embodiments, coaxial screw gear sleeve mechanisms include a post with a threaded exterior surface and a corresponding sleeve configured to surround the post, the corresponding sleeve having a threaded interior surface configured to interface with the threaded exterior surface of the post and a geared exterior surface. A drive mechanism can be configured to interface with the geared exterior surface of the sleeve, causing the device to expand.

22 Claims, 23 Drawing Sheets

Related U.S. Application Data continuation of application No. 14/318,196, filed on Jun. 27, 2014, now Pat. No. 9,474,626, which is a continuation of application No. 13/591,463, filed on Aug. 22, 2012, now Pat. No. 8,771,360, which is a continuation of application No. 12/841,465, filed on Jul. 22, 2010, now Pat. No. 8,303,663.

(60) Provisional application No. 61/365,131, filed on Jul. 16, 2010, provisional application No. 61/271,548, filed on Jul. 22, 2009.

(51) Int. Cl.
| | |
|---|---|
| *A61B 17/70* | (2006.01) |
| *A61F 2/46* | (2006.01) |
| *F16H 25/22* | (2006.01) |
| A61B 17/02 | (2006.01) |
| A61F 2/38 | (2006.01) |
| A61F 2/28 | (2006.01) |
| A61F 2/30 | (2006.01) |
| A61F 2/36 | (2006.01) |
| A61F 2/50 | (2006.01) |
| A61F 2/48 | (2006.01) |
| A61B 17/68 | (2006.01) |

(52) U.S. Cl.
CPC .......... *A61F 2/4455* (2013.01); *A61F 2/4611* (2013.01); *F16H 25/20* (2013.01); *F16H 25/2056* (2013.01); *F16H 25/2214* (2013.01); A61B 2017/0256 (2013.01); A61B 2017/681 (2013.01); A61F 2/385 (2013.01); A61F 2/3868 (2013.01); A61F 2/482 (2021.08); A61F 2002/2817 (2013.01); A61F 2002/2835 (2013.01); A61F 2002/3082 (2013.01); A61F 2002/30235 (2013.01); A61F 2002/30405 (2013.01); A61F 2002/30426 (2013.01); A61F 2002/30433 (2013.01); A61F 2002/30523 (2013.01); A61F 2002/30525 (2013.01); A61F 2002/30556 (2013.01); A61F 2002/30579 (2013.01); A61F 2002/30593 (2013.01); A61F 2002/30601 (2013.01); A61F 2002/30604 (2013.01); A61F 2002/30624 (2013.01); A61F 2002/30639 (2013.01); A61F 2002/30841 (2013.01); A61F 2002/30904 (2013.01); A61F 2002/30925 (2013.01); A61F 2002/3631 (2013.01); A61F 2002/448 (2013.01); A61F 2002/4628 (2013.01); A61F 2002/4629 (2013.01); A61F 2002/507 (2013.01); A61F 2002/5041 (2013.01); A61F 2002/5069 (2013.01); A61F 2220/0025 (2013.01); A61F 2220/0041 (2013.01); A61F 2230/0069 (2013.01); A61F 2240/001 (2013.01); A61F 2250/0009 (2013.01); A61F 2310/00023 (2013.01); A61F 2310/00029 (2013.01); A61F 2310/00796 (2013.01); A61F 2310/00976 (2013.01); A61F 2310/00982 (2013.01); A61F 2310/00988 (2013.01); A61F 2310/00994 (2013.01); F16H 2025/209 (2013.01); F16H 2025/2046 (2013.01); F16H 2025/2084 (2013.01); H05K 999/99 (2013.01); Y10T 29/49 (2015.01); Y10T 74/18608 (2015.01); Y10T 74/18672 (2015.01); Y10T 74/19702 (2015.01); Y10T 74/19749 (2015.01)

(56) References Cited

U.S. PATENT DOCUMENTS

| | | |
|---|---|---|
| 811,344 A | 1/1906 | Wands |
| 1,388,836 A | 8/1921 | Ripsch et al. |
| 1,500,859 A | 7/1924 | Wright |
| 1,547,946 A | 7/1925 | Myers |
| 2,106,088 A | 1/1938 | De Tar |
| 2,231,221 A | 2/1941 | Rector |
| 2,453,656 A | 11/1948 | Bullard |
| 2,666,334 A | 1/1954 | Nalle |
| 2,711,105 A | 6/1955 | Williams |
| 2,842,976 A | 7/1958 | Young |
| 2,891,408 A | 6/1959 | Burt, Jr. |
| 3,386,128 A | 6/1968 | Vyvyan |
| 3,449,971 A | 6/1969 | Posh |
| 3,575,475 A | 4/1971 | Boemer |
| 3,596,863 A | 8/1971 | Kaspareck |
| 3,597,938 A | 8/1971 | Hellen |
| 3,700,289 A | 10/1972 | Bilinski et al. |
| 3,700,290 A | 10/1972 | Ensinger |
| 3,708,925 A | 1/1973 | Ainoura |
| 3,709,132 A | 1/1973 | Farrell |
| 3,916,596 A | 11/1975 | Hawley |
| 3,985,000 A | 10/1976 | Hartz |
| 3,988,906 A | 11/1976 | Smith |
| 4,261,211 A | 4/1981 | Haberland |
| 4,396,047 A | 8/1983 | Balkus |
| 4,478,103 A | 10/1984 | Benjamin |
| 4,478,109 A | 10/1984 | Kobelt |
| 4,516,303 A | 5/1985 | Kloster |
| 4,528,864 A | 7/1985 | Craig |
| 4,559,717 A | 12/1985 | Scire |
| 4,630,495 A | 12/1986 | Smith |
| 4,691,586 A | 9/1987 | van Leijenhorst |
| 4,694,703 A | 9/1987 | Routson |
| 4,869,552 A | 9/1989 | Tolleson |
| 5,133,108 A | 7/1992 | Esnault |
| 5,172,442 A | 12/1992 | Bartley et al. |
| 5,181,371 A | 1/1993 | DeWorth |
| 5,196,857 A | 3/1993 | Chiappetta |
| 5,198,932 A | 3/1993 | Takamura |
| 5,222,986 A | 6/1993 | Wright |
| 5,313,852 A | 5/1994 | Arena |
| 5,374,556 A | 12/1994 | Bennett |
| 5,439,377 A | 8/1995 | Milanovich |
| 5,445,471 A | 8/1995 | Wexler et al. |
| 5,554,191 A | 9/1996 | Lahille et al. |
| 5,645,599 A | 7/1997 | Samani |
| 5,653,763 A | 8/1997 | Errico et al. |
| 5,664,457 A | 9/1997 | Nejati |
| 5,904,479 A | 5/1999 | Staples |
| 5,960,670 A | 10/1999 | Iverson |
| 5,980,252 A | 11/1999 | Samchukov |
| 5,988,006 A | 11/1999 | Fleytman |
| 6,039,761 A | 3/2000 | Li et al. |
| 6,045,579 A | 4/2000 | Hochshuler et al. |
| 6,056,491 A | 5/2000 | Hsu |
| 6,080,193 A | 6/2000 | Hochshuler et al. |
| 6,136,031 A | 10/2000 | Middleton |
| 6,175,989 B1 | 1/2001 | Carpentar et al. |
| 6,315,797 B1 | 11/2001 | Middleton |
| 6,350,317 B1 | 2/2002 | Hao et al. |
| 6,378,172 B1 | 4/2002 | Schrage |
| 6,395,035 B2 | 5/2002 | Bresina et al. |
| 6,454,806 B1 | 9/2002 | Cohen et al. |
| 6,454,807 B1 | 9/2002 | Jackson |
| 6,484,608 B1 | 11/2002 | Ziavras |
| 6,517,772 B1 | 2/2003 | Woolf |
| 6,554,526 B1 | 4/2003 | Egelandsdal |
| 6,616,695 B1 | 9/2003 | Crozet et al. |
| 6,641,614 B1 | 11/2003 | Wagner et al. |
| 6,719,796 B2 | 4/2004 | Cohen et al. |
| 6,752,832 B2 | 6/2004 | Neumann |
| 6,772,479 B2 | 8/2004 | Hinkley |
| 6,802,229 B1 | 10/2004 | Lambert |
| 6,808,537 B2 | 10/2004 | Michelson |
| 6,863,673 B2 | 3/2005 | Gerbec et al. |

(56) References Cited

U.S. PATENT DOCUMENTS

| | | |
|---|---|---|
| 6,932,844 B2 | 8/2005 | Ralph et al. |
| 6,953,477 B2 | 10/2005 | Berry |
| 7,018,415 B1 | 3/2006 | McKay |
| 7,051,610 B2 | 5/2006 | Stoianovici |
| 7,070,598 B2 | 7/2006 | Lim et al. |
| 7,087,055 B2 | 8/2006 | Lim et al. |
| 7,201,751 B2 | 4/2007 | Zucherman et al. |
| 7,273,373 B2 | 9/2007 | Horiuchi |
| 7,308,747 B2 | 12/2007 | Smith |
| 7,316,381 B2 | 1/2008 | Hacker |
| 7,410,201 B1 | 8/2008 | Wilson |
| 7,425,103 B2 | 9/2008 | Perez-Sanchez |
| 7,431,735 B2 | 10/2008 | Liu et al. |
| 7,435,032 B1 | 10/2008 | Murphey |
| 7,547,325 B2 | 6/2009 | Biedermann et al. |
| 7,584,682 B2 | 9/2009 | Hsiao |
| 7,611,538 B2 | 11/2009 | Belliard et al. |
| 7,632,281 B2 | 12/2009 | Errico et al. |
| 7,674,296 B2 | 3/2010 | Rhoda et al. |
| 7,682,376 B2 | 3/2010 | Frieu |
| 7,708,779 B2 | 5/2010 | Edie et al. |
| 7,712,389 B2 | 5/2010 | Wang |
| 7,753,958 B2 | 7/2010 | Gordon et al. |
| 7,758,645 B2 | 7/2010 | Studer |
| 7,758,648 B2 | 7/2010 | Castleman et al. |
| 7,892,285 B2 | 2/2011 | Viker |
| 7,896,919 B2 | 3/2011 | Belliard et al. |
| 7,901,409 B2 | 3/2011 | Canaveral et al. |
| 7,947,078 B2 | 5/2011 | Siegal |
| 7,985,256 B2 | 7/2011 | Grotz et al. |
| 8,057,549 B2 | 11/2011 | Butterman et al. |
| 8,070,813 B2 | 12/2011 | Grotz et al. |
| 8,088,163 B1 | 1/2012 | Kleiner |
| 8,142,441 B2 | 3/2012 | Refai et al. |
| 8,192,495 B2 | 6/2012 | Simpson et al. |
| 8,303,663 B2 | 11/2012 | Jimenez et al. |
| 8,496,706 B2 | 7/2013 | Ragab et al. |
| 8,523,944 B2 | 9/2013 | Jimenez et al. |
| 8,540,452 B2 | 9/2013 | Jimenez et al. |
| 8,628,577 B1 | 1/2014 | Jimenez |
| 8,636,746 B2 | 1/2014 | Jimenez et al. |
| 8,771,360 B2 | 7/2014 | Jimenez et al. |
| 8,795,366 B2 | 8/2014 | Varela |
| 8,894,712 B2 | 11/2014 | Varela |
| 8,906,100 B2 | 12/2014 | Jimenez |
| 8,932,302 B2 | 1/2015 | Jimenez et al. |
| 8,940,049 B1 | 1/2015 | Jimenez et al. |
| 9,358,125 B2 | 6/2016 | Jimenez et al. |
| 9,381,092 B2 | 7/2016 | Jimenez et al. |
| 9,445,917 B2 | 9/2016 | Jimenez et al. |
| 9,474,626 B2 | 10/2016 | Jimenez et al. |
| 9,486,328 B2 | 11/2016 | Jimenez |
| 9,498,270 B2 | 11/2016 | Jimenez et al. |
| 9,668,879 B2 | 6/2017 | Jimenez et al. |
| 9,867,717 B2 | 1/2018 | Jimenez |
| 10,117,757 B2 | 11/2018 | Jimenez et al. |
| 2002/0128716 A1 | 9/2002 | Cohen et al. |
| 2002/0138146 A1 | 9/2002 | Jackson |
| 2003/0077110 A1 | 4/2003 | Knowles |
| 2003/0233145 A1 | 12/2003 | Landry et al. |
| 2004/0049271 A1 | 3/2004 | Biedermann et al. |
| 2004/0111157 A1 | 6/2004 | Ralph |
| 2004/0153156 A1 | 8/2004 | Cohen et al. |
| 2004/0225364 A1 | 11/2004 | Richelsoph et al. |
| 2005/0000228 A1 | 1/2005 | De Sousa |
| 2005/0033431 A1 | 2/2005 | Gordon |
| 2005/0095384 A1 | 5/2005 | Wittmeyer |
| 2005/0113921 A1 | 5/2005 | An et al. |
| 2005/0113924 A1 | 5/2005 | Buttermann |
| 2005/0175406 A1 | 8/2005 | Perez-Sanchez |
| 2005/0182416 A1 | 8/2005 | Lim et al. |
| 2005/0261769 A1 | 11/2005 | Moskowitz et al. |
| 2006/0004447 A1 | 1/2006 | Mastrorio et al. |
| 2006/0004455 A1 | 1/2006 | Leonard et al. |
| 2006/0025862 A1 | 2/2006 | Villiers et al. |
| 2006/0058878 A1 | 3/2006 | Michelson |
| 2006/0129244 A1 | 6/2006 | Ensign |
| 2006/0149385 A1 | 7/2006 | McKay |
| 2006/0184171 A1 | 8/2006 | Biedermann et al. |
| 2006/0247781 A1 | 11/2006 | Francis |
| 2006/0253201 A1 | 11/2006 | McLuen |
| 2006/0293752 A1 | 12/2006 | Moumene |
| 2007/0032791 A1 | 2/2007 | Greenhalgh |
| 2007/0049943 A1 | 3/2007 | Moskowitz |
| 2007/0083267 A1 | 4/2007 | Miz et al. |
| 2007/0093901 A1 | 4/2007 | Grotz et al. |
| 2007/0129730 A1 | 6/2007 | Woods et al. |
| 2007/0185577 A1 | 8/2007 | Malek |
| 2007/0191954 A1 | 8/2007 | Hansell et al. |
| 2007/0191958 A1 | 8/2007 | Abdou |
| 2007/0198089 A1 | 8/2007 | Moskowitz |
| 2007/0219634 A1 | 9/2007 | Greenhalgh |
| 2007/0222100 A1 | 9/2007 | Husted |
| 2007/0250171 A1 | 10/2007 | Bonin |
| 2007/0255415 A1 | 11/2007 | Edie et al. |
| 2007/0282449 A1 | 12/2007 | de Villiers et al. |
| 2007/0288092 A1 | 12/2007 | Bambakidis |
| 2007/0293329 A1 | 12/2007 | Glimpel et al. |
| 2007/0293948 A1 | 12/2007 | Bagga et al. |
| 2008/0026903 A1 | 1/2008 | Flugrad |
| 2008/0077246 A1 | 3/2008 | Fehling |
| 2008/0091211 A1 | 4/2008 | Gately |
| 2008/0100179 A1 | 5/2008 | Ruggeri |
| 2008/0103601 A1 | 5/2008 | Biro et al. |
| 2008/0114367 A1 | 5/2008 | Meyer |
| 2008/0140207 A1 | 6/2008 | Olmos et al. |
| 2008/0147194 A1 | 6/2008 | Grotz et al. |
| 2008/0154266 A1 | 6/2008 | Protopsaltis |
| 2008/0161920 A1 | 7/2008 | Melkent |
| 2008/0161931 A1 | 7/2008 | Perez-Cruet |
| 2008/0168855 A1 | 7/2008 | Giefer |
| 2008/0183138 A1 | 7/2008 | Moser et al. |
| 2008/0183204 A1 | 7/2008 | Greenhalgh et al. |
| 2008/0188941 A1 | 8/2008 | Grotz |
| 2008/0210039 A1 | 9/2008 | Brun |
| 2008/0221694 A1 | 9/2008 | Warnick et al. |
| 2008/0234736 A1 | 9/2008 | Trieu |
| 2008/0281423 A1 | 11/2008 | Sheffer et al. |
| 2008/0292392 A1 | 11/2008 | Voellmer |
| 2008/0319487 A1 | 12/2008 | Fielding |
| 2009/0012564 A1 | 1/2009 | Chirico et al. |
| 2009/0076614 A1 | 3/2009 | Arramon |
| 2009/0099568 A1 | 4/2009 | Lowry et al. |
| 2009/0164017 A1 | 6/2009 | Sommerich |
| 2009/0210061 A1 | 8/2009 | Sledge |
| 2009/0222100 A1 | 9/2009 | Cipoletti et al. |
| 2009/0234362 A1 | 9/2009 | Blain et al. |
| 2009/0259316 A1 | 10/2009 | Ginn et al. |
| 2009/0299478 A1 | 12/2009 | Carls et al. |
| 2009/0306672 A1 | 12/2009 | Reindel et al. |
| 2010/0004688 A1 | 1/2010 | Maas |
| 2010/0076557 A1 | 3/2010 | Miller |
| 2010/0082109 A1 | 4/2010 | Greenhalgh |
| 2010/0094305 A1 | 4/2010 | Chang |
| 2010/0161062 A1 | 6/2010 | Foley et al. |
| 2010/0185291 A1 | 7/2010 | Jimenez et al. |
| 2010/0192715 A1 | 8/2010 | Vauchel et al. |
| 2010/0209184 A1 | 8/2010 | Jimenez |
| 2011/0015638 A1 | 1/2011 | Pischl et al. |
| 2011/0054616 A1 | 3/2011 | Kamran |
| 2011/0093075 A1 | 4/2011 | Duplessis |
| 2011/0112644 A1 | 5/2011 | Zilberstein |
| 2011/0138948 A1 | 6/2011 | Jimenez et al. |
| 2011/0160861 A1 | 6/2011 | Jimenez et al. |
| 2011/0172774 A1 | 7/2011 | Varela |
| 2011/0270398 A1 | 11/2011 | Grotz et al. |
| 2012/0010653 A1 | 1/2012 | Seifert et al. |
| 2012/0029636 A1 | 2/2012 | Ragab et al. |
| 2012/0116518 A1 | 5/2012 | Grotz et al. |
| 2012/0158071 A1 | 6/2012 | Jimenez et al. |
| 2012/0185049 A1 | 7/2012 | Varela |
| 2012/0226357 A1 | 9/2012 | Varela |
| 2012/0271419 A1 | 10/2012 | Marik |
| 2012/0290094 A1 | 11/2012 | Lim et al. |

(56) References Cited

U.S. PATENT DOCUMENTS

| | | |
|---|---|---|
| 2012/0303124 A1 | 11/2012 | McLuen et al. |
| 2012/0323329 A1 | 12/2012 | Jimenez et al. |
| 2013/0053966 A1 | 2/2013 | Jimenez et al. |
| 2013/0144388 A1 | 6/2013 | Emery et al. |
| 2013/0158664 A1 | 6/2013 | Palmatier et al. |
| 2013/0197642 A1 | 8/2013 | Ernst |
| 2013/0253650 A1 | 9/2013 | Ashley et al. |
| 2013/0317615 A1 | 11/2013 | Jimenez et al. |
| 2014/0012383 A1 | 1/2014 | Triplett et al. |
| 2014/0018924 A1 | 1/2014 | McManus et al. |
| 2014/0039622 A1 | 2/2014 | Glerum et al. |
| 2014/0088714 A1 | 3/2014 | Miller et al. |
| 2014/0140757 A1 | 5/2014 | Jimenez et al. |
| 2014/0156007 A1 | 6/2014 | Pabst et al. |
| 2014/0194991 A1 | 7/2014 | Jimenez |
| 2014/0236296 A1 | 8/2014 | Wagner et al. |
| 2014/0249628 A1 | 9/2014 | Weiman |
| 2014/0249629 A1 | 9/2014 | Moskowitz et al. |
| 2014/0288652 A1 | 9/2014 | Boehm et al. |
| 2014/0343608 A1 | 11/2014 | Whiton et al. |
| 2015/0025634 A1 | 1/2015 | Boehm et al. |
| 2015/0088258 A1 | 3/2015 | Jimenez et al. |
| 2015/0094814 A1 | 4/2015 | Emerick et al. |
| 2015/0100128 A1 | 4/2015 | Glerum et al. |
| 2015/0148908 A1 | 5/2015 | Marino et al. |
| 2015/0272743 A1 | 10/2015 | Jimenez et al. |
| 2015/0272745 A1 | 10/2015 | Jimenez et al. |
| 2015/0272746 A1 | 10/2015 | Jimenez et al. |
| 2015/0351925 A1 | 12/2015 | Emerick et al. |
| 2016/0262907 A1 | 9/2016 | Jimenez |
| 2016/0356368 A1 | 12/2016 | Jimenez et al. |
| 2018/0318107 A1 | 11/2018 | Cummins |

FOREIGN PATENT DOCUMENTS

| | | |
|---|---|---|
| EP | 1881209 B1 | 10/2008 |
| FR | 2372998 B1 | 12/1980 |
| JP | H0581194 B2 | 11/1993 |
| JP | 2004301135 A | 10/2004 |
| JP | 2007196792 A | 8/2007 |
| JP | 2008208932 A | 9/2008 |
| WO | 2004026188 A2 | 4/2004 |
| WO | 2004109155 A1 | 12/2004 |
| WO | 2005081330 A2 | 9/2005 |
| WO | 2005096975 A2 | 10/2005 |
| WO | 2006094535 A1 | 9/2006 |
| WO | 2006116052 A2 | 11/2006 |
| WO | 2006125329 A1 | 11/2006 |
| WO | 2007002583 A2 | 1/2007 |
| WO | 2007009107 A2 | 1/2007 |
| WO | 2007028140 A2 | 3/2007 |
| WO | 2007076377 A2 | 7/2007 |
| WO | 2007111979 A2 | 10/2007 |
| WO | 2008137192 A1 | 11/2008 |
| WO | 2009018349 A2 | 2/2009 |
| WO | 2010078468 A2 | 7/2010 |
| WO | 2010078520 A2 | 7/2010 |
| WO | 2011011626 A2 | 1/2011 |
| WO | 2011011609 A3 | 6/2011 |
| WO | 2014066890 A1 | 5/2014 |

OTHER PUBLICATIONS

Alexander H. Slocum, Fundamentals of Design (2005).
Amelie Jeanneau, et al., A Compliant Rolling Contact Joint and its Application in a 3-DOF Planar Parallel Mechanism with Kinematic Analysis, ASME, Design Engineering Technical Conferences, 9 pages, 2004.
Canadian Application No. 2,768,867, Office Action dated Apr. 19, 2017, 4 pages.
Canadian Application No. 2,768,867, Office Action dated Aug. 4, 2016, 4 pages.
Chou et al., Efficacy of Anterior Cervical Fusion: Comparison of Titanium Cages, polyetheretherketone (PEEK) cages and autogenous bone grafts, Journal of Clinical Neuroscience, 2008, pp. 1240-1245.
European Application No. EP 09837185, European Search Report dated May 14, 2013, 7 pages.
European Application No. EP 10802916.6, Examination Report dated May 12, 2016, 4 pages.
First Examination Report issued in corresponding Indian Application No. 952/DELNP/2012 dated Sep. 27, 2018.
Hunter et al., Overview of Medical Devices, Department of Radiology, University of Arizona, Aug. 2001, pp. 89-140, vol. 30, No. 4, ISSN: 0363-0188.
International Search Report and Written Opinion of the International Searching Authority or the Declaration dated Nov. 29, 2010, International Application No. PCT/US2009/069958, filed Dec. 31, 2009, 9 pages.
International Search Report and Written Opinion of the International Searching Authority or the Declaration dated Sep. 27, 2010, International Application No. PCT/US2009/069876, filed Dec. 30, 2009, 12 pages.
International Search Report, Application No. PCT/US2010/042915, dated Apr. 22, 2011.
Japanese Application No. 2012-521784, JP Office Action dated Feb. 18, 2014, 8 pages.
Just L. Herder, Force Directed Design of Laparoscopic Forceps, ASME Design Engineering Technical Conference, 8 pages, 1998.
Medtronic Sofamor Danek USA, Inc., CAPSTONE Instrument Set Technique, http://www.mtortho.com/public/capstone.pdf, .COPYRGT. 2005, 25 pages.
Medtronic, CAPSTONE Peek Spinal System Surgical Technique, http://www.mtortho.com/public/capstone_peek_st.pdf, .COPYRGT. 2009, 36 pages.
Notification of Transmittal of the International Search Report and the Written Opinion of the International Searching Authority or the Declaration,Application No. PCT/US2010/042941, dated Apr. 25, 2011.
PCT/US2009/069876, filed Dec. 30, 2009, International Search Report and Written Opinion dated Sep. 27, 2010, 10 pages.
PCT/US2009/069876, filed Dec. 30, 2009, International Search Report and Written Opinion dated Sep. 27, 2010, 12 pages.
PCT/US2009/069958, filed Dec. 31, 2009, International Search Report and Written Opinion dated Nov. 29, 2010, 7 pages.
PCT/US2009/069958, filed Dec. 31, 2009, International Search Report and Written Opinion dated Nov. 29, 2010, 9 pages.
PCT/US2010/042915, filed Jul. 22, 2010, Search Report and Written Opinion dated Apr. 22, 2011.
PCT/US2010/042941, filed Jul. 22, 2010, International Search Report and Written Opinion, dated Apr. 25, 2011.
PCT/US2013/067070, PCT Written Opinion/Search Report dated Feb. 27, 2014, 14 pages.
PCT/US2014/052913, PCT Written Opinion/Search Report dated Dec. 22, 2014, 10 pages.
PCT/US2015/032977, filed May 28, 2015, International Search Report and Written Opinion dated Sep. 21, 2015, 10 pages.
PCT/US2015/055449, filed Oct. 14, 2015, International Search Report and Written Opinion dated Dec. 11, 2015, 9 pages.
Peter A. Halverson, et al., Tension-based Multi-stable Compliant: Rolling-contact Elements, Department of Mechanica Engineering, Brigham Young University, Provo UT, USA 84602 (34 pages), 2007.
Printout from Video for OmniLIF Anterior Insertion Approach from Lumber Jax; https://seelio.com/w/fgf/omnilif-the-new-standard-in-spinal-deformit- y-correction-and-fusion?student=lumbarjax; dated Nov. 27, 2014, 7 pages.
Printout from Video for OmniLIF Features from Lumber Jax; https://seelio.com/w/fgf/omnilif-the-new-standard-in-spinal-deformity-cor- rection-and-fusion?student=lumbarjax; dated Nov. 27, 2014, 11 pages.
W. Kusswetter, A Supplementary Instrumentation for Posterior Fusion of Spine in Scoliosis, Archives of Orthopedic Traumatic Surgery, 1980, 1 page.
Website printout from https://seelio.com/w/fgf/omnilif-the-new-standard-in-spinal-deformity-cor-rection-and-fusion?student=lumbarjax; dated Nov. 27, 2014, 5 pages.

(56) References Cited

OTHER PUBLICATIONS

Wenzel Spine, Inc., VariLift.RTM.-L Expandable Interbody Fusion Device: A proven solution for stand-alone fusion, Product Overview, 12 pages, .COPYRGT. 2010.

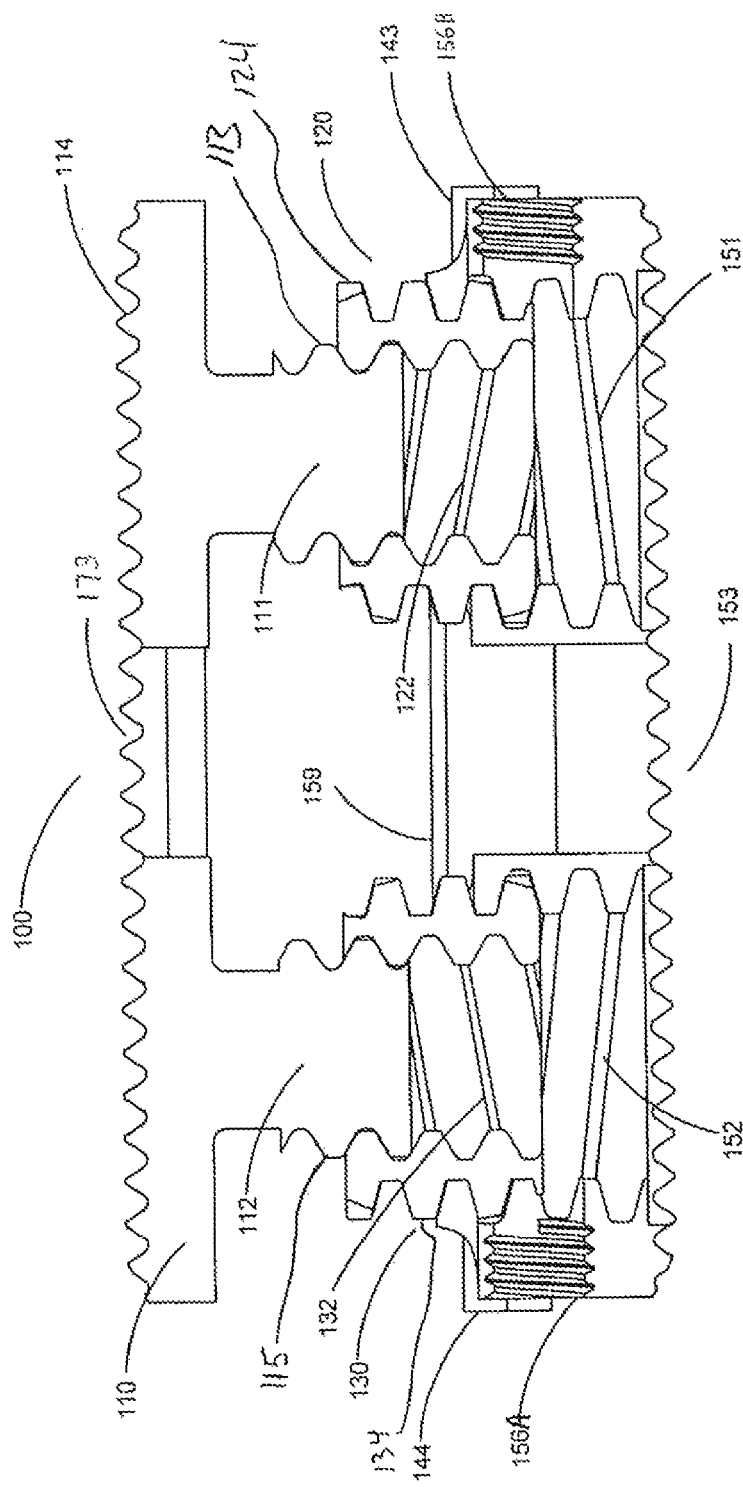

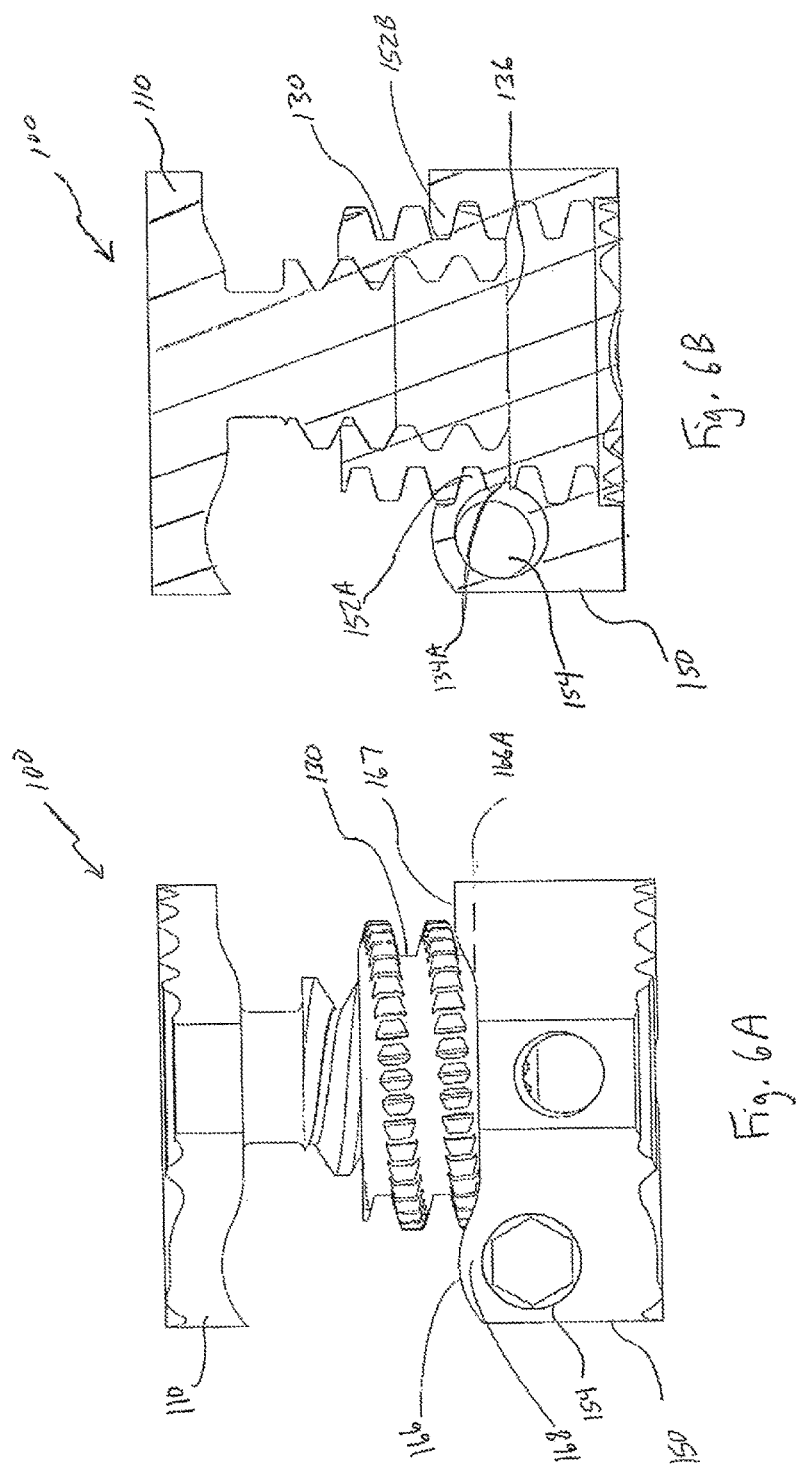

MEDICAL DEVICE EMPLOYING A COAXIAL SCREW GEAR SLEEVE MECHANISM

CROSS-REFERENCE TO RELATED APPLICATIONS

This application is a continuation of U.S. application Ser. No. 15/332,066, filed Oct. 24, 2016, which is a continuation of U.S. application Ser. No. 14/318,196, filed Jun. 27, 2014, which is a continuation of U.S. application Ser. No. 13/591,463, filed Aug. 22, 2012, which is a continuation of U.S. application Ser. No. 12/841,465 filed Jul. 22, 2010, which claims the benefit of U.S. Provisional Application No. 61/271,548 filed Jul. 22, 2009 and U.S. Provisional Application No. 61/365,131, filed Jul. 16, 2010, the disclosures of which are hereby incorporated herein by reference in their entirety.

FIELD OF THE INVENTION

The present invention relates to the distraction and fusion of vertebral bodies. More specifically, the present invention relates to devices and associated methods for distraction and fusion of vertebral bodies that utilize coaxial screw gear sleeve mechanisms.

BACKGROUND OF THE INVENTION

The concept of intervertebral fusion for the cervical and lumbar spine following a discectomy was generally introduced in the 1960s. It involved coring out a bone graft from the hip and implanting the graft into the disc space. The disc space was prepared by coring out the space to match the implant. The advantages of this concept were that it provided a large surface area of bone to bone contact and placed the graft under loading forces that allowed osteoconduction and induction enhancing bone fusion. However, the technique is seldom practiced today due to numerous disadvantages including lengthy operation time, destruction of a large portion of the disc space, high risk of nerve injury, and hip pain after harvesting the bone graft.

Presently, at least two devices are commonly used to perform the intervertebral portion of an intervertebral body fusion: the first is the distraction device and the second is the intervertebral body fusion device, often referred to as a cage. Cages can be implanted as standalone devices or as part of a circumferential fusion approach with pedicle screws and rods. The concept is to introduce an implant that will distract a collapsed disc and decompress the nerve root, allow load sharing to enhance bone formation and to implant a device that is small enough to allow implantation with minimal retraction and pulling on nerves.

In a typical intervertebral body fusion procedure, a portion of the intervertebral disc is first removed from between the vertebral bodies. This can be done through either a direct open approach or a minimally invasive approach. Disc shavers, pituitary rongeours, curettes, and/or disc scrapers can be used to remove the nucleus and a portion of either the anterior or posterior annulus to allow implantation and access to the inner disc space. The distraction device is inserted into the cleared space to enlarge the disc space and the vertebral bodies are separated by actuating the distraction device. Enlarging the disc space is important because it also opens the foramen where the nerve root exists. It is important that during the distraction process one does not over-distract the facet joints. An intervertebral fusion device is next inserted into the distracted space and bone growth factor, such as autograft, a collagen sponge with bone morphogenetic protein, or other bone enhancing substance may be inserted, either before or after insertion of the device into the disc space, into the space within the intervertebral fusion device to promote the fusion of the vertebral bodies.

Intervertebral fusion and distraction can be performed through anterior, posterior, oblique, and lateral approaches. Each approach has its own anatomic challenges, but the general concept is to fuse adjacent vertebra in the cervical thoracic or lumbar spine. Devices have been made from various materials. Such materials include cadaveric cancellous bone, carbon fiber, titanium and polyetheretherketone (PEEK). Devices have also been made into different shapes such as a bean shape, football shape, banana shape, wedge shape and a threaded cylindrical cage.

It is important for a device that is utilized for both intervertebral body fusion and distraction to be both small enough to facilitate insertion into the intervertebral space and of sufficient height to maintain the normal height of the disc space. Use of an undersized device that cannot expand to a sufficient height can result in inadequate fusion between the adjacent vertebrae and lead to further complications for the patient, such as migration of the device within or extrusion out of the disc space. Addressing these issues can require the use of multiple devices of varying sizes to be used serially to expand the disc space the proper amount, which increases the time required to carry out the procedure, increasing the cost and risk associated with the procedure.

Accordingly, there is a need in the art for a device of sufficient strength that can distract from a beginning size small enough to initially fit into the disc space to a height sufficient to reestablish and maintain the normal height of the disc space.

SUMMARY OF THE INVENTION

Improved methods and apparatuses for vertebral body distraction and fusion in accordance with various embodiments of the present invention employ one or more coaxial screw gear sleeve mechanisms. In various embodiments, coaxial screw gear sleeve mechanisms includes a post with a threaded exterior surface and a corresponding sleeve configured to surround the post, the corresponding sleeve having a threaded interior surface configured to interface with the threaded exterior surface of the post and a geared exterior surface. A drive mechanism can be configured to interface with the geared exterior surface of the sleeve, causing the device to distract.

In one embodiment, a device is used for both intervertebral distraction and fusion of an intervertebral disc space. The device can include a first bearing surface and a second bearing surface with at least one coaxial screw gear sleeve mechanism disposed in between. The coaxial screw gear sleeve mechanism includes a post with a threaded exterior surface projecting inwardly from one of the bearing surfaces and a corresponding sleeve configured to surround the post. The sleeve can project inwardly from the other of the bearing surfaces and have a threaded interior surface configured to interface with the threaded exterior surface of the post and a geared exterior surface. The device can further include a drive mechanism having a surface configured to interface with and drive the geared exterior surface of the sleeve, which causes a distraction of the first bearing surface and the second bearing surface.

In another embodiment, a method of intervertebral body distraction and fusion involves implantation of a distractible intervertebral body fusion device into an intervertebral disc space. The device is inserted such that a first bearing surface interfaces with an end plate of a superior vertebra of the intervertebral disc space and a second bearing surface interfaces with an end plate of an inferior vertebra of the disc space. At least one coaxial screw gear sleeve mechanism is disposed between the bearing surfaces and includes a threaded post, a corresponding sleeve having an interior thread mating with the threaded post and an exterior gear mating with a drive mechanism. The method includes distracting the device from a collapsed configuration to an expanded configuration by operating the drive mechanism to rotate the sleeve relative to the post, thereby expanding the first bearing surface with respect to the second bearing surface.

The above summary of the various embodiments of the invention is not intended to describe each illustrated embodiment or every implementation of the invention. This summary represents a simplified overview of certain aspects of the invention to facilitate a basic understanding of the invention and is not intended to identify key or critical elements of the invention or delineate the scope of the invention.

BRIEF DESCRIPTION OF THE DRAWINGS

The invention may be more completely understood in consideration of the following detailed description of various embodiments of the invention in connection with the accompanying drawings, in which:

FIG. 1D is a partial sectional view of the distractible intervertebral body fusion device of FIG. 1A.

FIG. 6A is an end view of a distractible intervertebral body fusion device according to an embodiment of the present invention.

FIG. 6B is a cross-sectional end view of the distractible intervertebral body fusion device of FIG. 6A taken looking into the page.

Figure 1A:
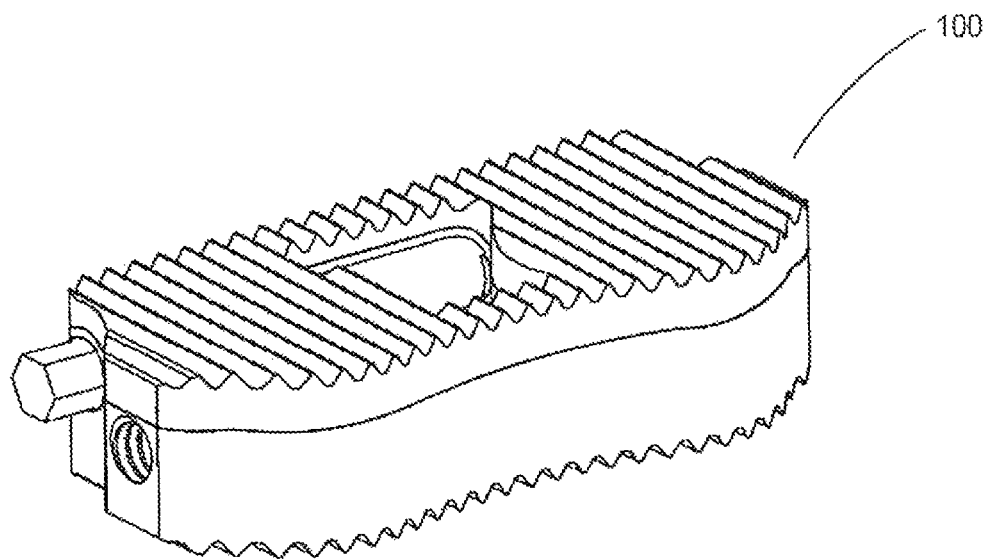
FIG. 1A is perspective view of a distractible intervertebral body fusion device according to an embodiment of the present invention in a collapsed configuration.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

In the following detailed description of the present invention, numerous specific details are set forth in order to provide a thorough understanding of the present invention. However, one skilled in the art will recognize that the present invention may be practiced without these specific details. In other instances, well-known methods, procedures, and components have not been described in detail so as to not unnecessarily obscure aspects of the present invention.

Figure 1B:
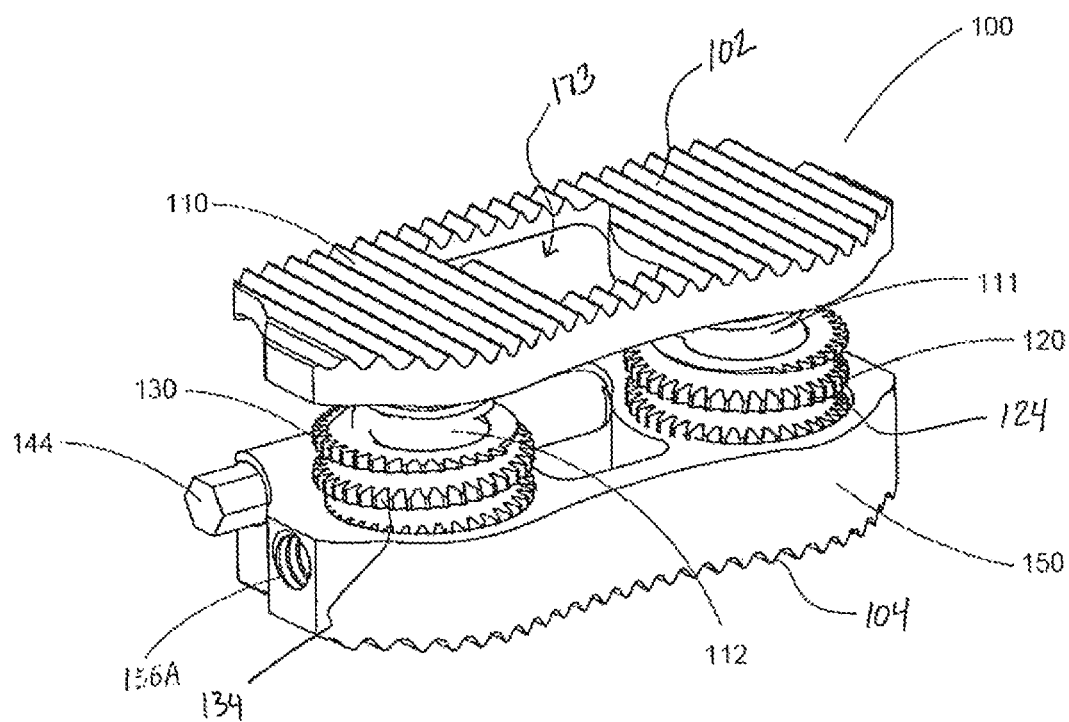
FIG. 1B is a perspective view of the distractible intervertebral body fusion device of FIG. 1A in an expanded configuration.
Figure 1C:
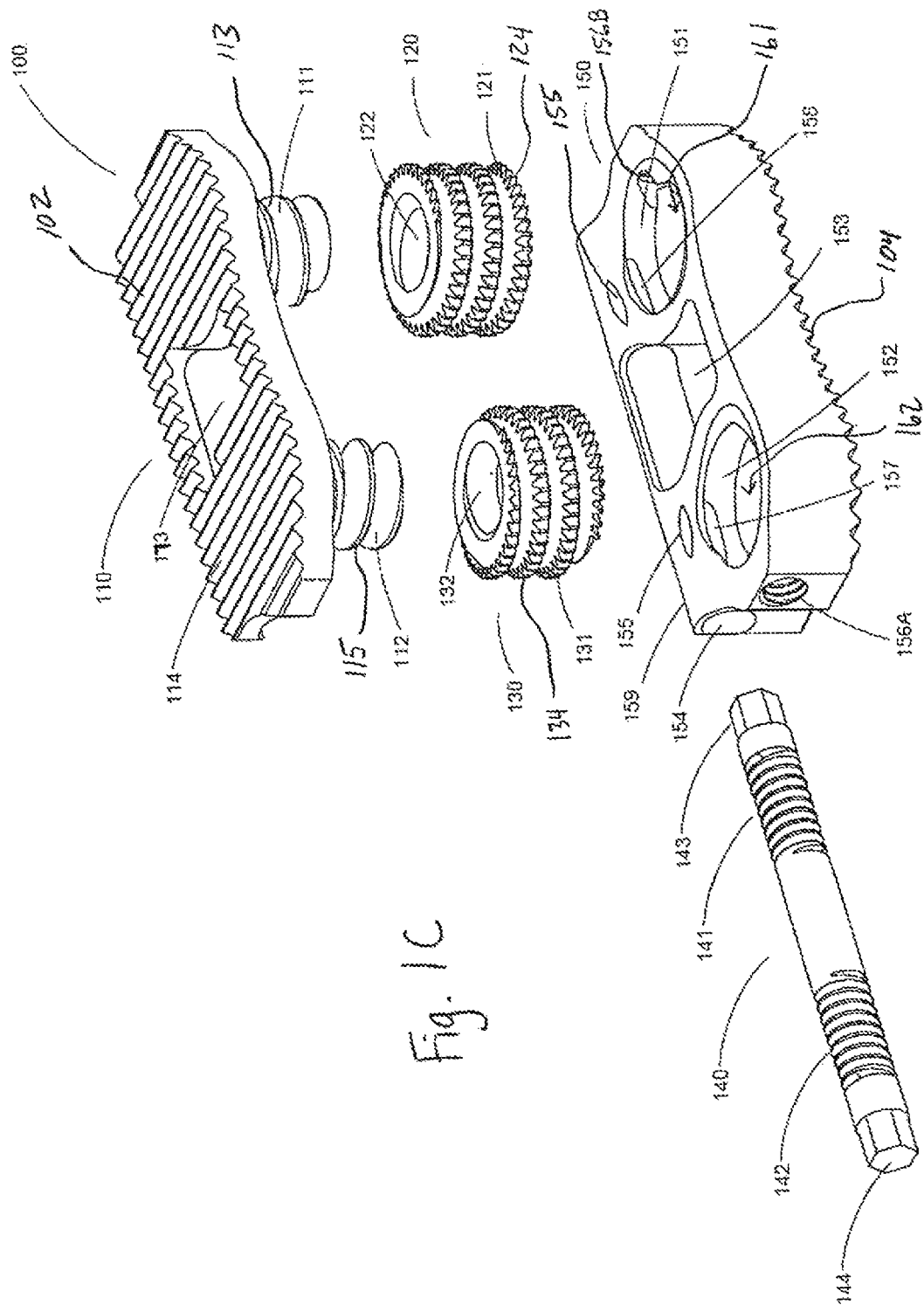
FIG. 1C is an exploded view of the distractible intervertebral body fusion device of FIG. 1A.

Referring to FIGS. 1A-1C, there can be seen a distractible intervertebral body fusion device 100 adapted for implantation into an intervertebral disc space of a patient according to an embodiment of the present invention. FIG. 1A shows the device 100 in a fully compressed configuration, FIG. 1B shows the device 100 in a fully expanded configuration, and FIG. 1C shows an exploded view of the device 100.

Device 100 includes a first member 110 having a bearing surface 102 configured to interface with an end plate of one of a superior or an inferior vertebra of the intervertebral disc space and a second member 150 having a bearing surface 104 configured to interface with an end plate of the other of the superior or inferior vertebra. In one embodiment, the bearing surfaces 102, 104 can include a textured surface, such as that provided by corrugations 114, to create friction with the end plates of the vertebra to prevent accidental extrusion of the device 100. The radii of the corrugation 114 valley and the corrugation 114 top width can be maximized to minimize the notch factor and reduce stress while still providing a corrugation design that reduces the propensity of the device 100 to extrude from the disc space. One or both of the members 110, 150, can also include an opening 173, 153 extending through the member for facilitating bone growth through the device 100. In other embodiments, opening can be filled with a gel, rubber, or other complaint material that can replicate the nucleus of an intervertebral disc and supplement the strength of the device in compressive, shear, and torsional loading conditions. Alternatively, a generally solid surface, a textured or etched surface, a scored or notched surface, or a surface with multiple openings can be provided on each member 110, 150

Device 100 can also include a pair of coaxial screw gear sleeve mechanisms including threaded post members 111, 112 extending from first member 110 and a pair of threaded geared sleeves 120, 130 configured to surround the post members 111, 112. Threaded post members 111, 112 can have threads 113, 115 defined on an exterior surface thereof. Threaded geared sleeves 120, 130 can have both interior threads 122, 132 configured to interface with the threads 113, 115 of threaded post members 111, 112 and exterior threads 121, 131. In one embodiment, both the exterior 121 and interior 122 threads of one of the sleeves 120 are of an opposite hand to the threads 131, 132 of the other sleeve 130. External threads 121, 131 of sleeves 120, 130 can have gear teeth 124, 134 cut into the thread. In one embodiment, the gear teeth 124, 134 are not cut down to the root, or minor diameter, of the threads 121, 131 in order to maximize the strength of the threads. In the compressed configuration, threaded geared sleeves 120, 130 can fit within sleeve openings of 161, 162 in second member 150. Openings 161, 162 can include threaded portions 151, 152 that mesh with exterior threads 121, 131 of threaded geared sleeves 120, 130. In one embodiment, sleeve openings 161, 162 extend all the way through bearing surface 104 of second member 150. In some embodiments, as pictured, threaded geared sleeves 120, 130 can be substantially solid. In other embodiments, threaded geared sleeves can include one or more slots through the sleeve for mass reduction and material savings or to promote bone in-growth.

The device 100 can be expanded with the aid of a worm 140 that extends through a worm aperture 154 in the device 100. The worm 140 can have first 142 and second 141 opposing threaded sections configured to interface with the exterior threads having gear teeth 124, 134 of threaded geared sleeves 120, 130 through a pair of apertures 157, 158 in threaded portions 151, 152 of sleeve openings 161, 162. The worm 140 can include a hex 143, 144 at each end of the worm 140 that allows it to be driven by a delivery system (described below). Such a delivery system can also be attached to the device 100 when driving the worm 140 at tapped hole 156A or tapped hole 156B to stabilize the delivery system. Device 100 can include a hex 143, 144 and tapped hole 156A, 156B at each end of device, so that the device 100 can be inserted and driven from either end, or can include a hex and tapped hole at only one side of the device, limiting the device to insertion and distraction from a single direction. Bottom member 150 can also include one or more scallops 155 above the worm aperture 154 that provide increased strength and thickness while still allowing the threaded geared sleeves 120, 130 to rotate.

A partial sectional view of a distractible intervertebral body fusion device 100 in FIG. 1D, helps illustrate how the device can employ multiple coaxial screw gear sleeve mechanisms as telescoping mechanisms utilizing the threaded post members 111, 112, threaded geared sleeves 120, 130 and the worm 140 to expand the first member 110 and second member 150 relative to each other. By turning hex 144 counterclockwise, and therefore the worm 140 counterclockwise, first threaded section 142 of worm 140 pulls the gear teeth 134 of threaded geared sleeve 130 towards the hex head 144. This causes the sleeve 130 to translate upward from the second member 150 along internal threads 152. As the sleeve 130 rotates while it translates upward, the threaded post member 112 extending from the first member 110, which is unable to turn, also translates upward with respect to the sleeve 130 and the second member 150. This second translation results from the opposite handed external threads 115 of the threaded post member 112 being driven by the matching internal threads 132 of the sleeve 130. The same mechanics are occurring on the other side of the device with oppositely threaded sleeve 120 having external threads 121 and internal threads 122, post member 111 having external threads 113 and second threaded section 141 of worm 140.

Because the threads for like components for each device are opposite handed, the threads 142 on one side of the worm 140 will be pulling the gear teeth 134 of the threaded geared sleeve 130 while the threads 141 on the other side of the worm 140 will be pushing the gear teeth 124 on the other sleeve 120, or vice versa depending on the direction of rotation of the worm 140. These opposing forces applied to the worm 140 by the threaded geared sleeves 120, 130 are carried in either tension or compression by the worm 140. Therefore, the worm 140 is not substantially driven into or out of the worm aperture 154 as the device 100 is expanded or contracted. This is advantageous in that a pin or other retainer is not required to retain the worm and balance the forces in the device. Such a pin can be a point of excessive wear which can cause the life cycle of the device to be shorter lived. In some embodiments, a pin can be employed to prevent the worm 140 from being able to be pulled or pushed axially, which can cause the device to become jammed.

Alternative drive mechanisms to worm drive include piezoelectric actuators and any momentum imparting collision mechanism or configuration. Additionally, a drive mechanism, such as a worm, could be an integrated part of a delivery system. In such an embodiment, the external threads of the threaded geared sleeves would both be of the same hand and the worm would be screwed into the compressed device in the worm aperture. As the worm is turned, the axial position of the worm would be constrained by the delivery system, instead of a pin, resulting in distraction of the device. Once the device reached the desired height, the worm could be screwed out of the worm aperture and the device could be locked in place by screwing in a threaded locking worm. The locking worm could have an additional threaded or snapping feature that enables it to be permanently, or in a removable fashion, attached to the device. The locking worm could be made from a radio transparent material such as PEEK, which would therefore allow imaging through the worm. The locking worm would only need to be strong enough to inhibit the threaded geared sleeves from turning into or out of the device, and would not need to be strong enough to cause the device to distract. A larger radio transparent window could be formed by removing a portion of the sides of the bottom member on either side of the opening in the bottom member along the length of the device, so long as the device retained a necessary amount of stiffness.

Figure 2A:
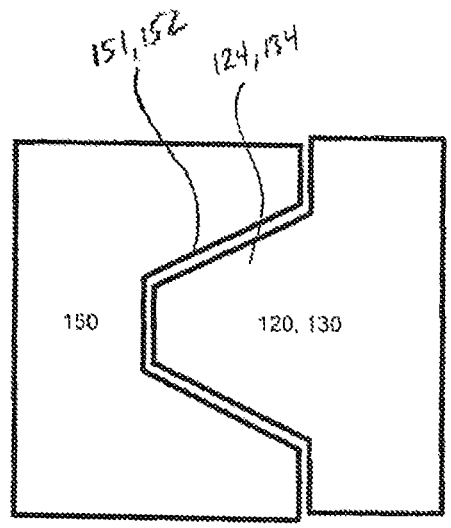
FIG. 2A is a partial side view of a distractible intervertebral body fusion device according to an embodiment of the present invention.
Figure 2B:
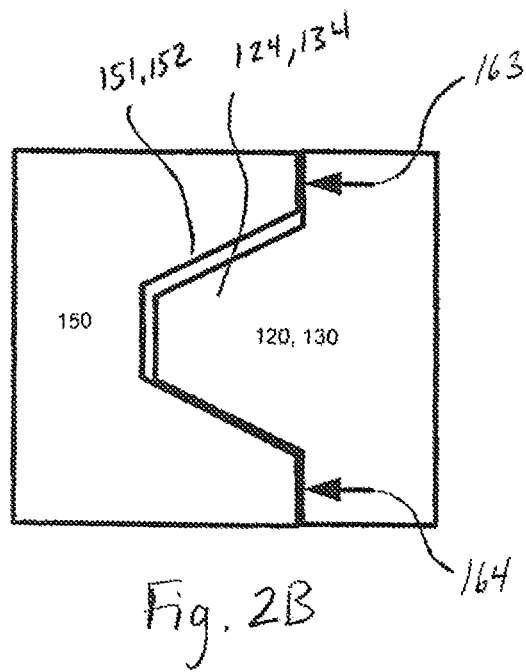
FIG. 2B is a partial side view of the distractible intervertebral body fusion device of FIG. 2A.
Figure 3A:
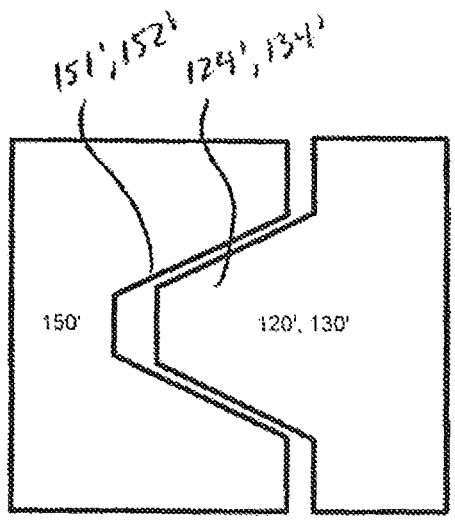
FIG. 3A is a partial side view of a distractible intervertebral body fusion device according to an embodiment of the present invention.
Figure 3B:
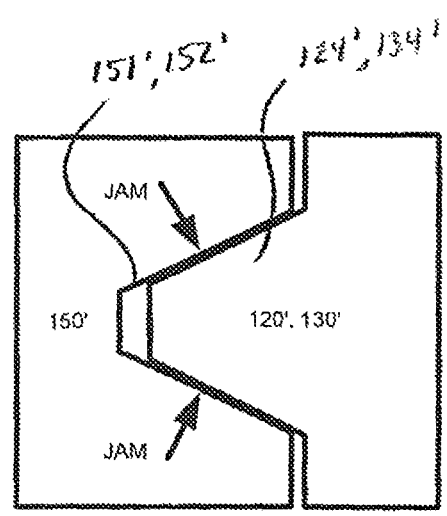
FIG. 3B is a partial side view of the distractible intervertebral body fusion device of FIG. 3A.

Referring now to FIGS. 2A and 2B, a preferred fit of gear teeth 124, 134 of threaded geared sleeves 120, 130 in internal threaded portions, 151, 152 of second member 150 is shown. As the gear teeth 124, 134 are thrust towards the internal threads 151, 152 of the second member 150 by the worm, the load between the gear teeth 124, 134 and threads 151, 152 is balanced by the bearing surfaces 163, 164 between the components, which results in the ability of the device 100 to distract a substantial load. This fit between the gear teeth 124, 134 and the internal threads 151, 152 can be contrast with the fit shown in FIGS. 3A and 3B. In those figures, when the gear teeth 124', 134' of the threaded geared sleeves 120', 130' are thrust towards the internal threads 151', 152' of the second member 150', the force is not balanced by bearing surfaces as in FIG. 2B, but by the force the internal threads 151', 152' apply to the gear teeth 124', 134'. This can result in the gear teeth 124', 134' acting as a wedge and becoming jammed against the internal threads 151', 152', which dramatically reduces the ability of the device to distract substantial loads and makes the device more sensitive to friction between components. Optionally, a liquid or gas lubricant, such as silicon lubricant, may be used to reduce friction in the mechanism. Saline may also be used as a lubricant.

It should be noted that although the threads depicted in the Figures are all screw threads in the form of projecting helical ribs, "thread" for the purposes of the present invention can also refer to any other mechanism that translates rotational force into translational or longitudinal movement. For example, in some embodiments threads can be comprised of a recirculating or spiral arrangement of bearings or any other low friction arrangement, such as cooperating magnets.

In one embodiment, the height of the device 100 between the bearing surfaces 102, 104 in the fully compressed configuration is 6.5 millimeters and the maximum fully distracted height is 12 millimeters, thus providing a very large amount of distraction relative to the initial height of the device. The maximum height is defined by the largest height at which the device can meet the dynamic compressive, shear, and torsional requirements for implantable intervertebral body fusion devices. Variables that determine this height include the width of the threaded geared sleeves, which is limited by the desired width of the device, and the material from which the device is made. With regard to the material for the device, materials with higher fatigue performance allow the maximum height of the device to be taller even with a narrower width. In one embodiment, the device is made from titanium. The device may also be made from cobalt chrome, MP35N, or PEEK, for increased strength characteristics or increased radiolucent characteristics, depending on the material. X-ray transparency is a desirable property because it allows for the fusing bone to be imaged through the device. In one embodiment, the device can be designed such that in the compressed configuration the threaded geared sleeves project through the bearing surface of second member in order to provide for an even greater amount of distraction. To accommodate the device on implantation, openings configured to contain the projecting portions of the sleeves can be cut into the adjacent vertebral end plate.

Once distracted, device 100 does not require a locking mechanism to maintain the desired height within the body. This is because, when driven backwards, the device exhibits a very high gear ratio which causes even the slightest friction in the system to overwhelm any amount of compression, torsion, or shear loading that might be applied to the device. In dynamic testing in shear, torsion, and compression, the maximum amount by which the height of the device changed was by approximately 0.01 millimeter. The device 100, because height can be maintained at any point along the threaded geared sleeves, therefore also exhibits very high resolution height control, on the order of 1 micrometer.

Figure 4A:
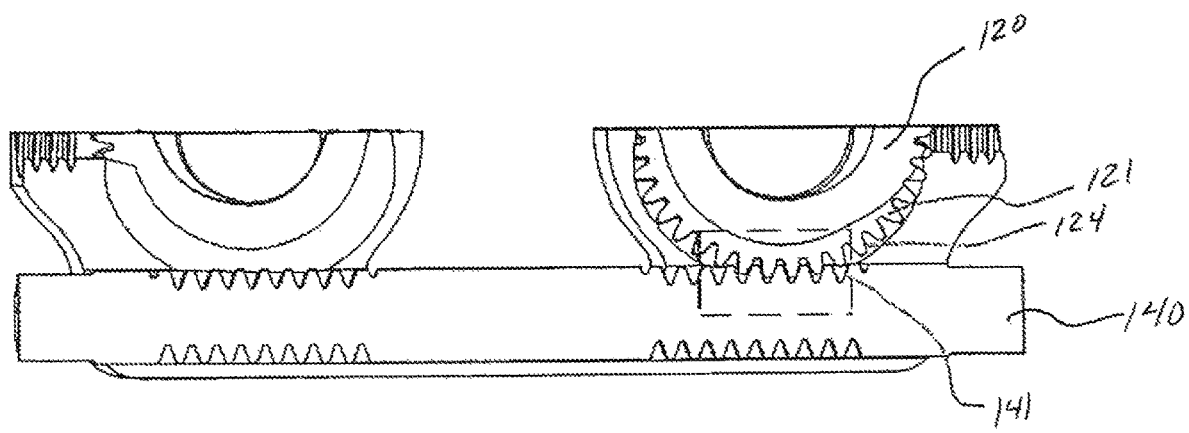
FIG. 4A is a partial top view of a distractible intervertebral body fusion device according to an embodiment of the present invention.
Figure 4B:
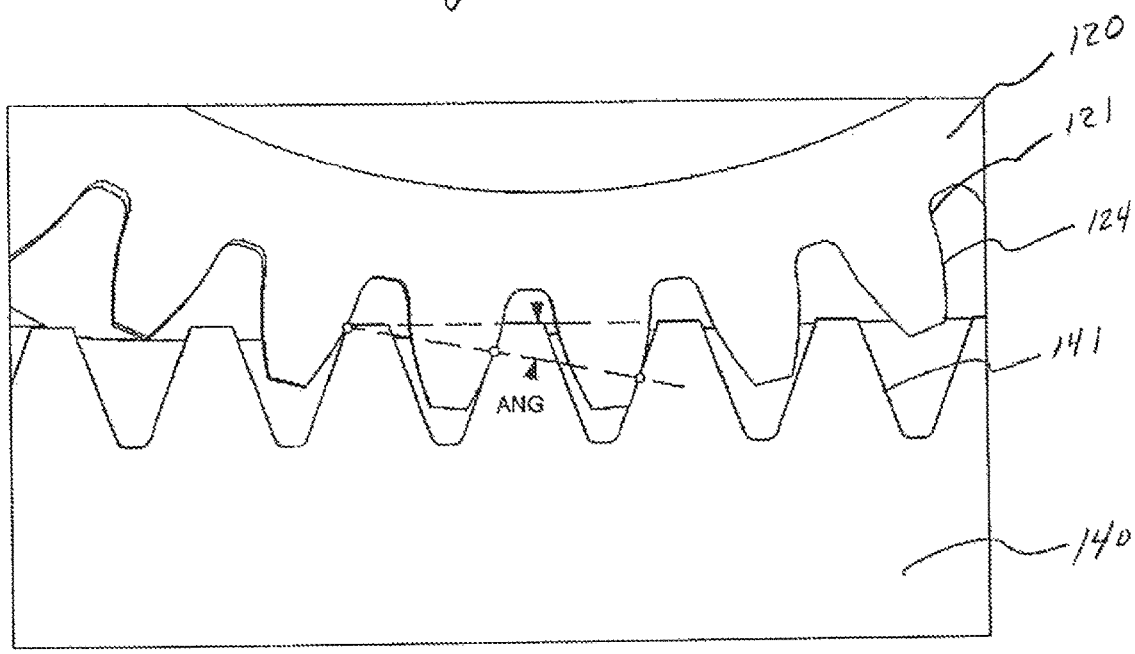
FIG. 4B is a partial top view of the distractible intervertebral body fusion device of FIG. 4A.

In one embodiment, the external threads 121, 131 and gear teeth 124, 134 on the threaded geared sleeves 120, 130 can be substantially trapezoidal in shape. In one embodiment, the thread is a trapezoidal 8 millimeter by 1.5 millimeter metric thread. A trapezoidal design enables a relatively large gear tooth size and, accordingly, a larger area over which the distraction loading is distributed. Additionally, with precise manufacturing, multiple gear teeth 124, 134 on the threaded geared sleeves 120, 130 can be engaged by the worm 140 at the same time along the pressure angle ANG, as shown in FIGS. 4A and 4B. Distributing the distraction load over multiple teeth of the sleeves 120, 130 and the worm 140 is critical to achieve the minimum device size while providing a maximum amount of distraction and load capacity.

Figure 5A:
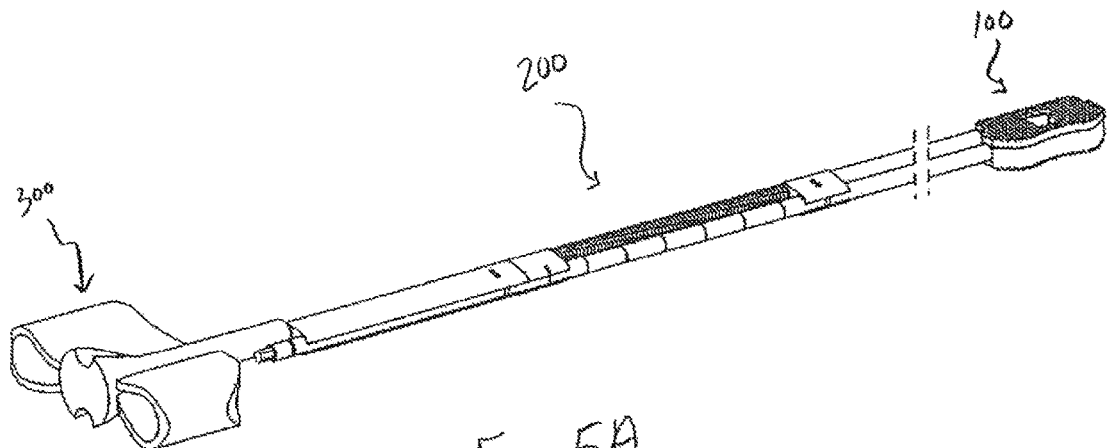
FIG. 5A is a perspective view of an insertion tool and a distractible intervertebral body fusion device according to an embodiment of the present invention.
Figure 5B:
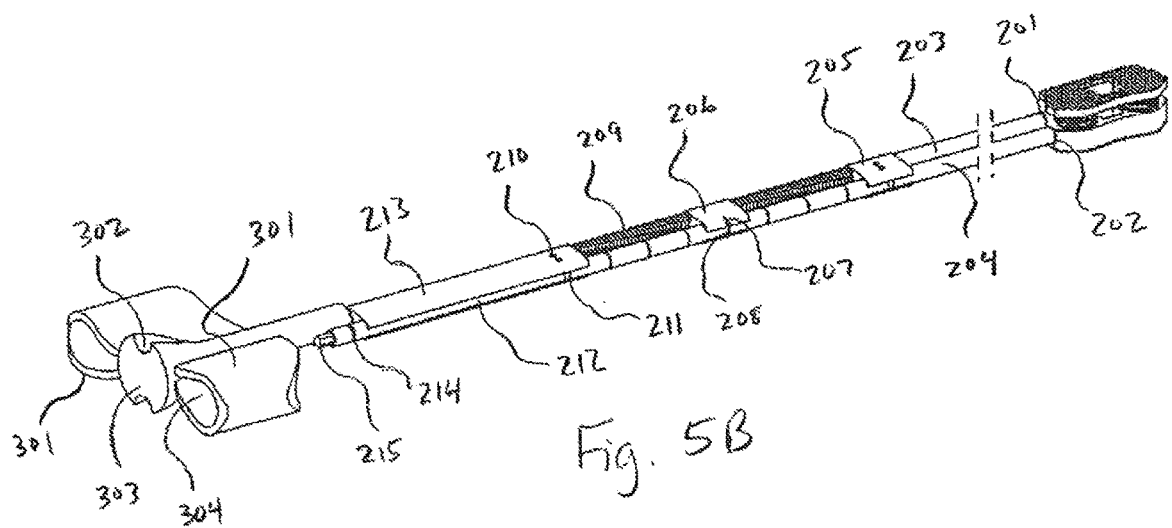
FIG. 5B is a perspective view of an insertion tool and a distractible intervertebral body fusion device according to an embodiment of the present invention.
Figure 5C:
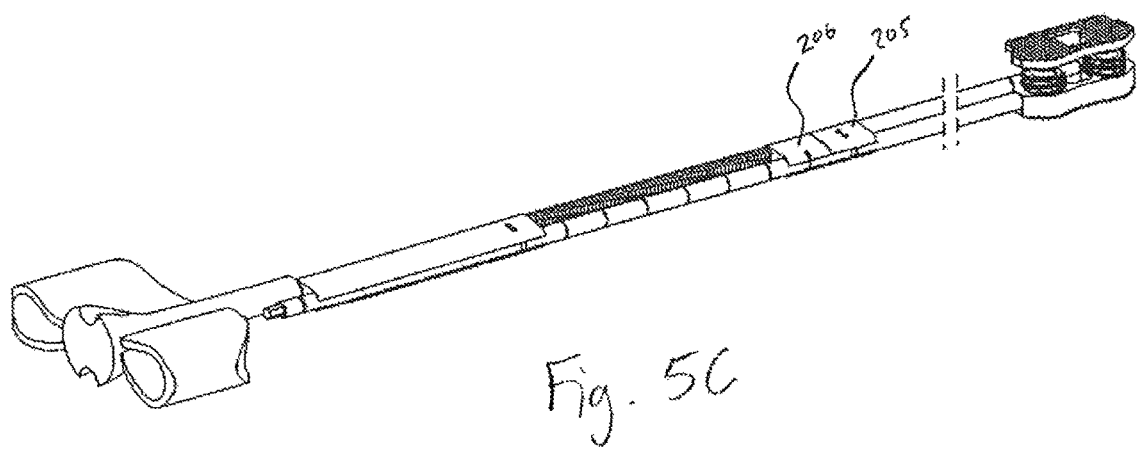
FIG. 5C is a perspective view of an insertion tool and a distractible intervertebral body fusion device according to an embodiment of the present invention.

A delivery system 200 for implanting a distractible intervertebral body fusion device according to an embodiment of the present invention is depicted in FIGS. 5A (compressed configuration), 5B (partially distracted configuration, and 5C (fully distracted configuration). Delivery system 200 also includes an actuation tool 300 for actuating the distraction.

To distract the device 100, a hex 143 or 144 of device is first connected to the delivery system 200 via a socket driver on an end 201 of delivery shaft 203. In order to more securely attach the device 100 and the delivery system 200, a threaded end 202 of delivery shaft 204 can be threaded into one of tapped holes 156A or 156B in second member 150 of device 100. The device 100 can then be inserted into the body via a standard transforaminal lumbar interbody fusion (TLIF) or posterior lumbar interbody fusion (PLIF) procedure using the delivery system 200. A lateral interbody fusion through the lateral retroperitoneal corridor is another approach. The delivery system 200 can guide the location of the device 100 as it is being inserted with use of handle 213.

Delivery system 200 includes a hex 215 and a circumferential groove 214 at the near end of delivery shaft 204, and also has a hex and circumferential groove (not pictured) at the end of delivery shaft 203. Once the device 100 is in the disc space, the actuation tool 300 can be connected to the delivery system by engaging an internal hex socket driver of the actuation tool with the hex on the end of the delivery shaft 203, 204. In some embodiments, an internal snap ring or circumferential spring in actuation tool 300 can engage the circumferential groove on delivery shaft 203 to ensure that the actuation tool 300 does not become accidentally disengaged during use.

Figure 5D:
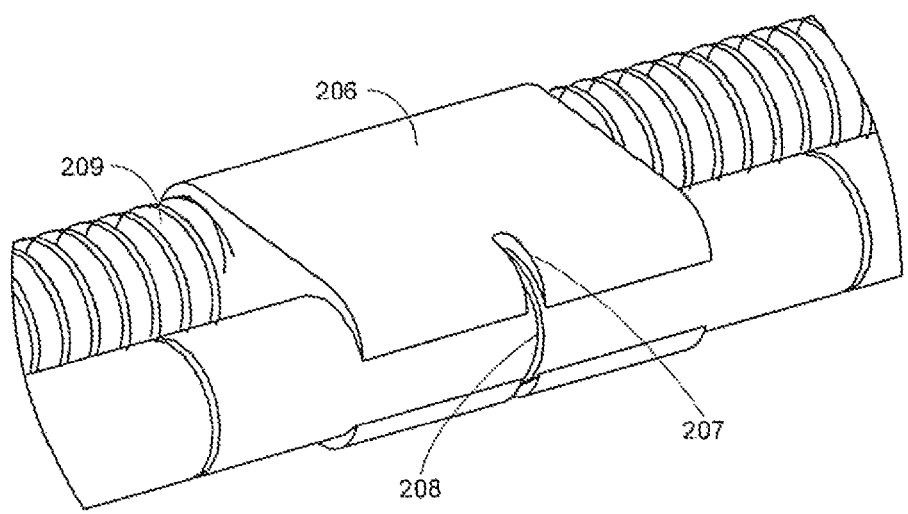
FIG. 5D is a partial perspective view of an insertion tool according to an embodiment of the present invention.

By turning the actuation tool 300, the user transmits torque down the delivery shaft 203 to the worm 140, which distracts the device 100. As the delivery shaft 203 is turned, a slider 206 advances along threads 209 on shaft 203. The height of the device 100 as it is expanded can be represented on the delivery system 200 by the position of the slider 206 along the delivery shaft 204 with fiducial marks 208, as shown best in FIG. 5D. Marks 208 may be positioned at any desirable interval along delivery shaft 204, and the slider 206 may include a viewing slot 207 for more complete viewing of the marks 208 as they are reached by slider 206. In one embodiment, each mark 208 can represent a distracted height of 1 millimeter.

Delivery system 200 can be configured so that when the device 100 reaches its maximum desired height, slider 206 abuts stop 205 so that it can be advanced no further, thus limiting the height of the device 100. By allowing the delivery system 200 to limit the expansion, any damage due to excessive torque is immediately apparent in the delivery system 200, so no damage is sustained by the device 100. In another embodiment, the device 100 can limit its own expansion by welding two of the gear teeth 124, 134 on one of the threaded geared sleeves 120, 130 together so that they bind with the worm 140 when the device 100 has reached its maximum desired height. Similarly, in other embodiments, one or more of the gear teeth 124, 134 can be omitted or a small post can be inserted into the interstitial space between two gear teeth to limit the expansion of the device.

In one embodiment, a lever for applying torque to the shaft 204 may be affixed to the hex 215 at the end of shaft 204. The lever may be shaped and oriented such that when the device 100 is appropriately engaged with the delivery system 200, the position of the lever allows access to the drive shaft 203, whereas when the device is not appropriately engaged, the lever does not allow access to the drive shaft 203. In another embodiment, the slider 206 may be contained with the handle 213 in order to reduce the length of the delivery system 200. In another embodiment, a tube able to carry loading in torsion may be implemented around one of the shafts 203, 204 to add to the structural rigidity of the delivery system. A small foot may be affixed to the tube to additionally support the ability of the delivery system to carry, and transmit, loading in torsion by and to the device. In another embodiment, the shaft of the delivery system 200 can be curved or bayonet in shape to allow visualization through a minimally invasive system and working channel.

The actuation tool 300 can include a recess or loop 304 that allows that user to spin the actuation tool 300 with a single finger and/or large gripping surfaces 301 that the user can grasp to turn the actuation tool 300. In one embodiment, the loop may be lined with a slippery or bearing surface to enable the loop to spin easily around the user's gloved finger(s). The actuation tool 300 can also include a broad surface 303 designed to receive the impact of a hammer for implantation. Recesses 302 can also be included on actuation tool 300 to afford the user an improved view of the device 100 while it is being implanted. Actuation tool 300 can span both delivery shafts 203, 204 and may extend over and/or receive handle 213 of delivery system 200. In another embodiment, rather than being driven by manual actuation tool 300, the device 100 can be driven by a powered actuation implement such as a pneumatic or electric drill or a motorized screwdriver mechanism, which, in some embodiments, can allow the tool to be controlled remotely.

In other embodiments, the actuation tool, manual or automatic, employs sensors in the device to transmit data regarding the implantation parameters and environment, such as device load and muscular tension, to an operator or operating system to improve the performance of the surgical procedure and outcome. The delivery system 200 could use small strain gauges located on the device 100 and/or load cells attached to the delivery shafts 203, 204 and actuation tool to measure loads present during the implantation and distraction process. These gauges and/or load cells could be monitored by a microcontroller board located on the delivery system 200 and the information fed back to a monitoring computer via a standard interface such as a USB or wireless connection. This information could be used to closely monitor a procedure's progress, warn of impending problems and improve future procedures. If not fully bridged, the gauges could be configured as half bridges within the device and completed outside of the device. Standard signal conditioning amplifiers could be used to excite and condition the signal to yield a measurable output of voltage and current.

In one embodiment, the device 100 can have a strengthened second member 150 as shown in FIGS. 6A and 6B. This can be done by lowering the worm aperture 154, and therefore the worm 140, such that when the device 100 is expanded to its full height, the worm 140 engages a full gear tooth 134A on the threaded geared sleeve 130 closest to the bottom 136 of the threaded geared sleeve 130. This allows a top surface 166 of the second member 150 to be lowered, which allows the first member 110 to be thicker, and therefore stronger, while maintain the same initial height In addition, this allows the material 168 between the top surface 166 of the second member 150 and the worm aperture 154 to be made thicker. A further advantage of this configuration is that at least one full internal thread 152A of the second member 150 is in engagement with the threaded geared sleeve 134 when the device is fully distracted. In such a configuration, an additional thickness 167 can be added to the side of second member 150 opposite of the worm aperture 154 to what was previously described as the top surface 166A of that side of the second member 150. This allows for a full internal thread 152B to engage the threaded geared sleeve 130 on the side opposite of internal thread 152A. By capturing the threaded geared sleeve with a full thread on both sides, when the device is loaded with shear and torsion, a maximum amount of material is resisting the load, which minimizes the resulting stress and increases the fatigue life of the device 100.

Figure 7A:
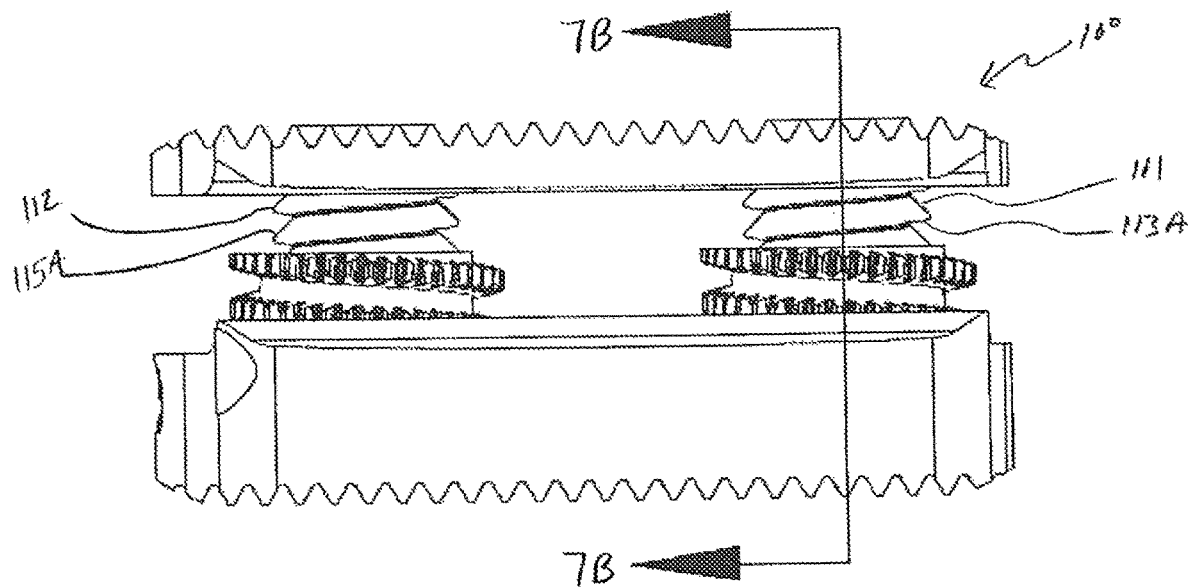
FIG. 7A is a front view of a distractible intervertebral body fusion device according to an embodiment of the present invention.
Figure 7B:
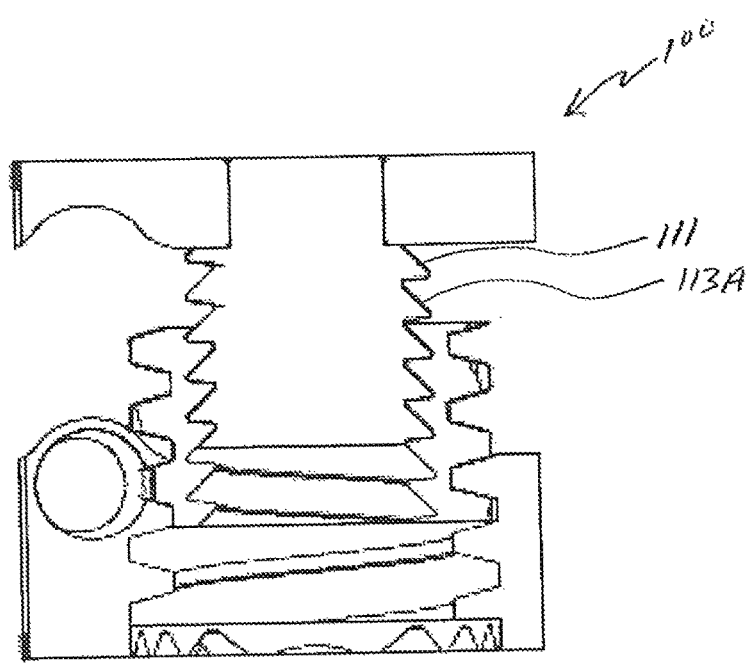
FIG. 7B is a cross-sectional view of the distractible intervertebral body fusion device of FIG. 7A taken along the lines 7B-7B.
Figure 8A:
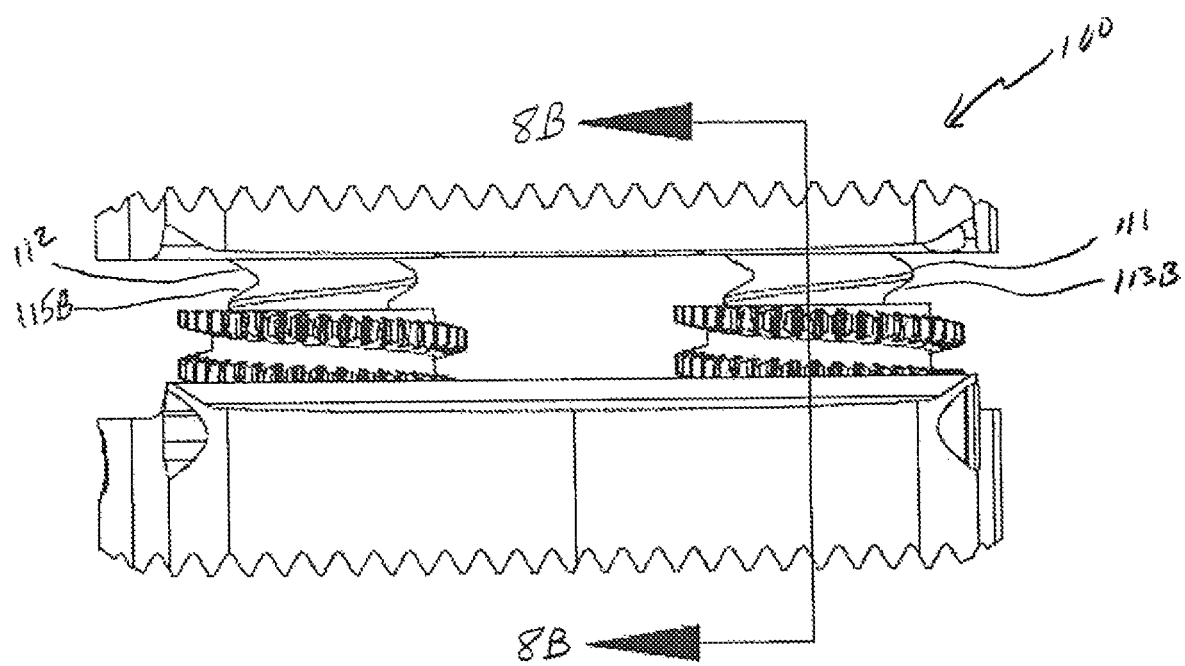
FIG. 8A is a front view of a distractible intervertebral body fusion device according to an embodiment of the present invention.
Figure 8B:
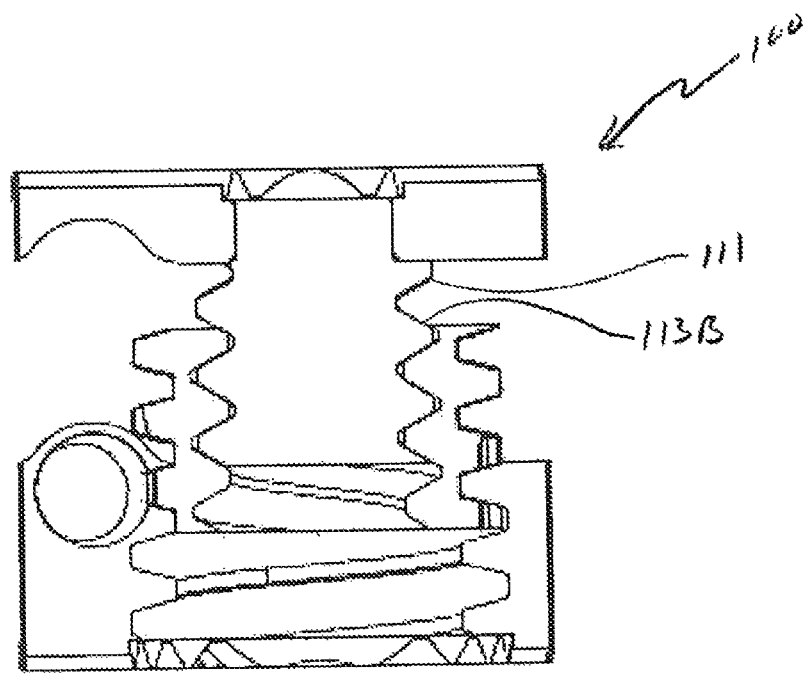
FIG. 8B is a cross-sectional view of the distractible intervertebral body fusion device of FIG. 8A taken along the lines 8A-8A.

FIGS. 7A and 7B depict another embodiment of the present invention where in threaded posts 111, 112 employ a buttress thread 113A, 115A (compare threads 113A in FIG. 7B to threads 113, 115 in FIG. 1D). A buttress thread configuration results in the load bearing thread face being perpendicular to the screw axis of the post 111, 112, which increases the axial strength of the device. FIGS. 8A and 8B depict a further embodiment that utilizes a standard 60 degree thread 113B, 115B on threaded posts 111, 112. 60 degree threads are considered industry standard and can therefore be created with common machining practices. This can result in a device that can be more quickly and inexpensively produced.

Figure 9A:
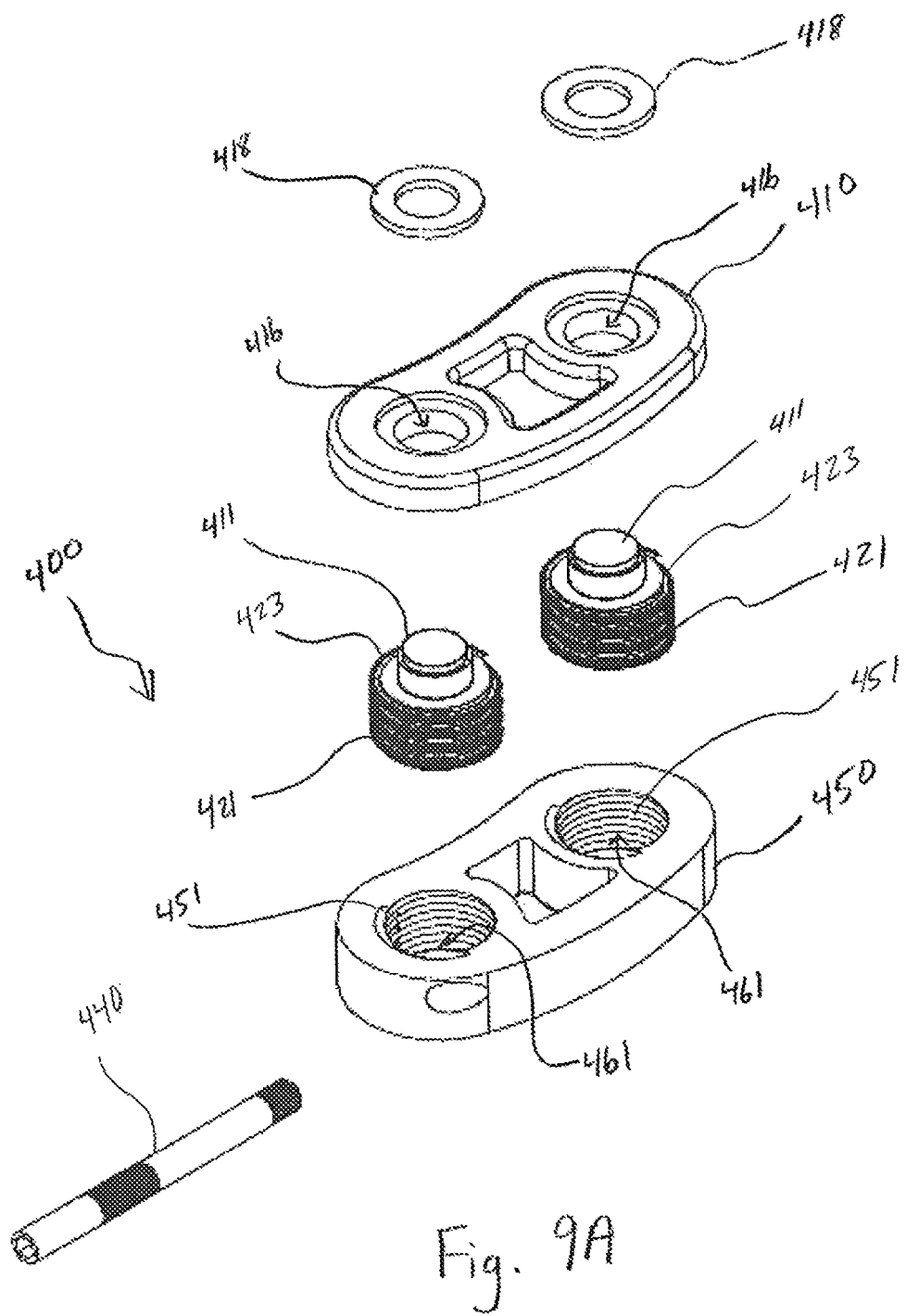
FIG. 9A is an exploded view of a distractible intervertebral body fusion device according to an embodiment of the present invention.
Figure 9B:
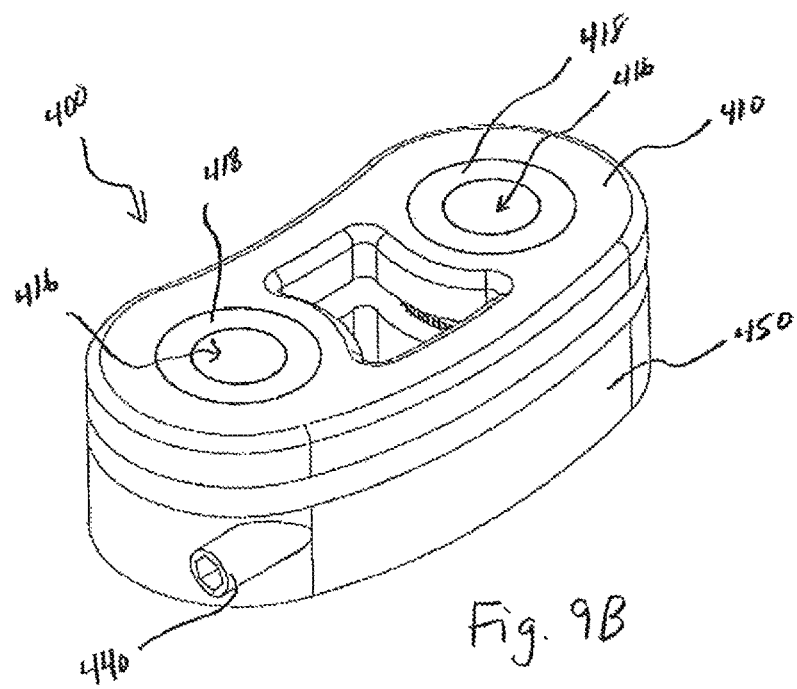
FIG. 9B is a perspective view of the distractible intervertebral body fusion device of FIG. 9A.
Figure 9C:
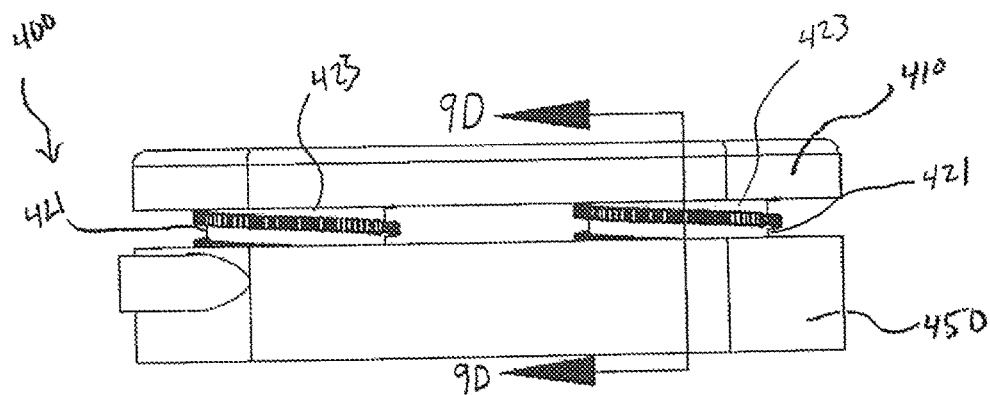
FIG. 9C is a front view of the distractible intervertebral body fusion device of FIG. 9A.
Figure 9D:
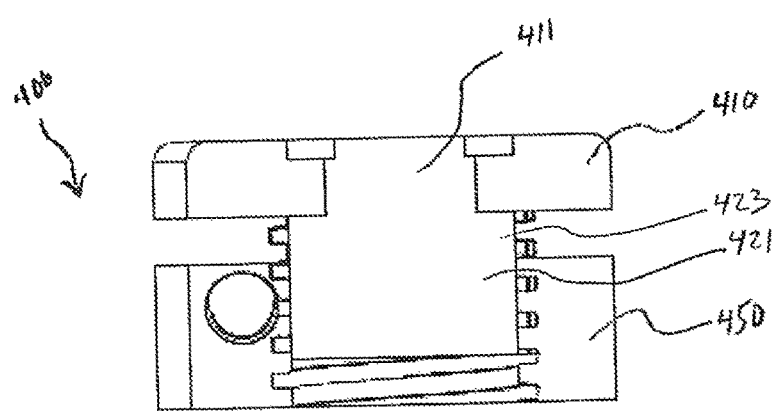
FIG. 9D is a cross-sectional view of the distractible intervertebral body fusion device of FIG. 9A taken along the lines 9D-9D in FIG. 9C.
Figure 10A:
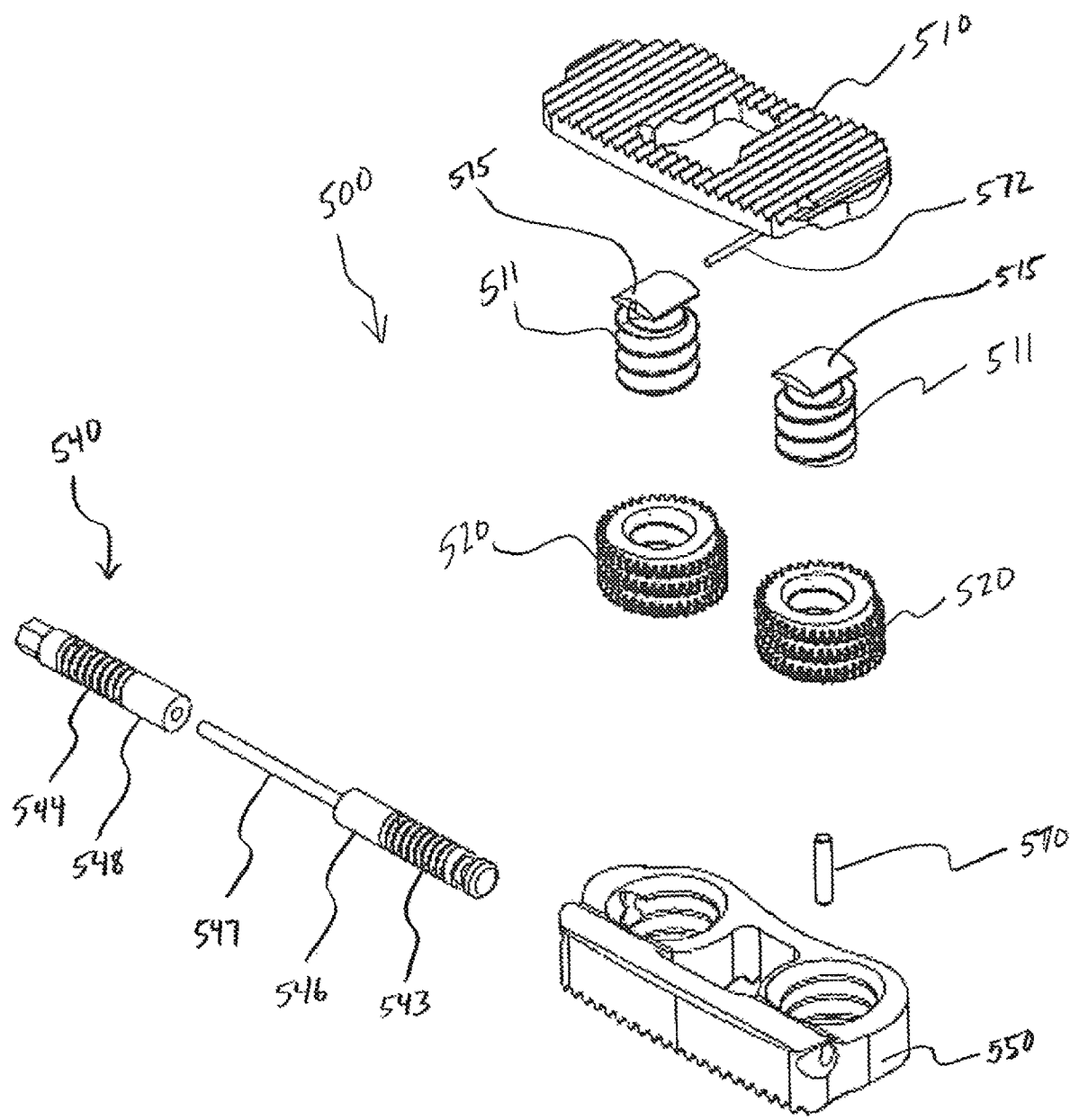
FIG. 10A is an exploded view of a distractible intervertebral body fusion device according to an embodiment of the present invention.
Figure 10B:
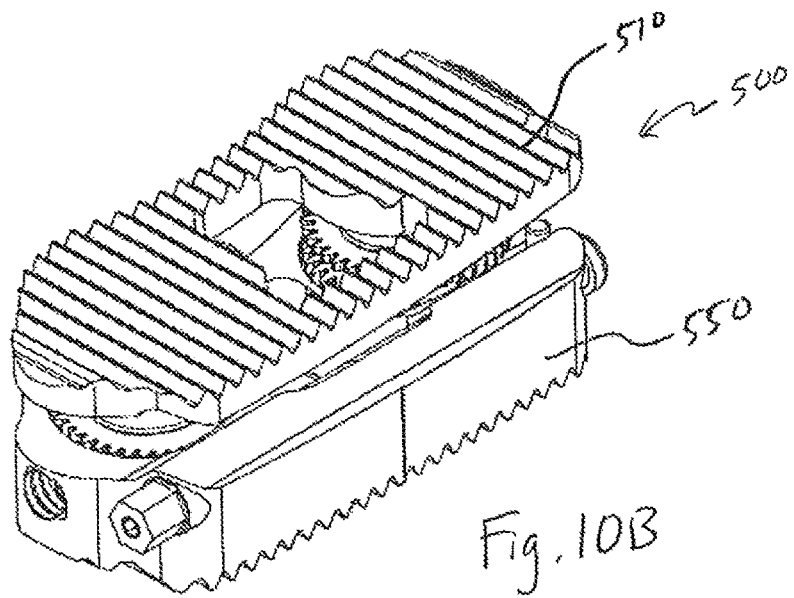
FIG. 10B is a perspective view of the distractible intervertebral body fusion device of FIG. 10A.
Figure 10C:
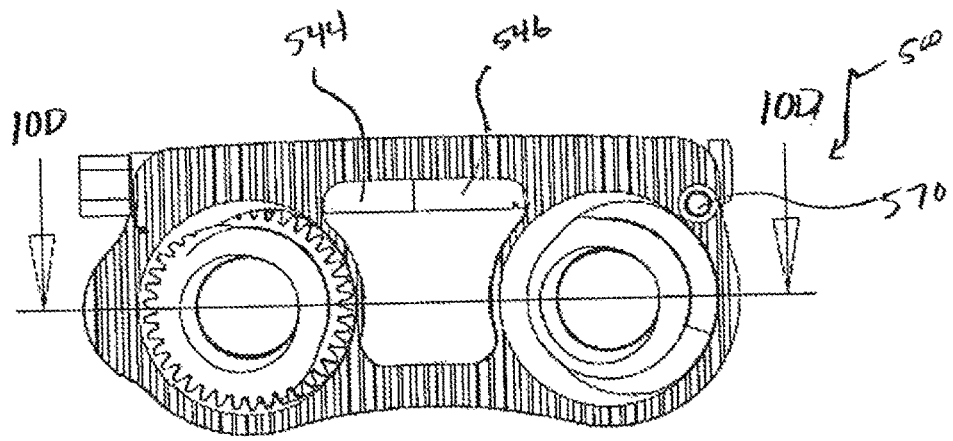
FIG. 10C is a bottom view of the distractible intervertebral body fusion device of FIG. 10A.
Figure 10D:
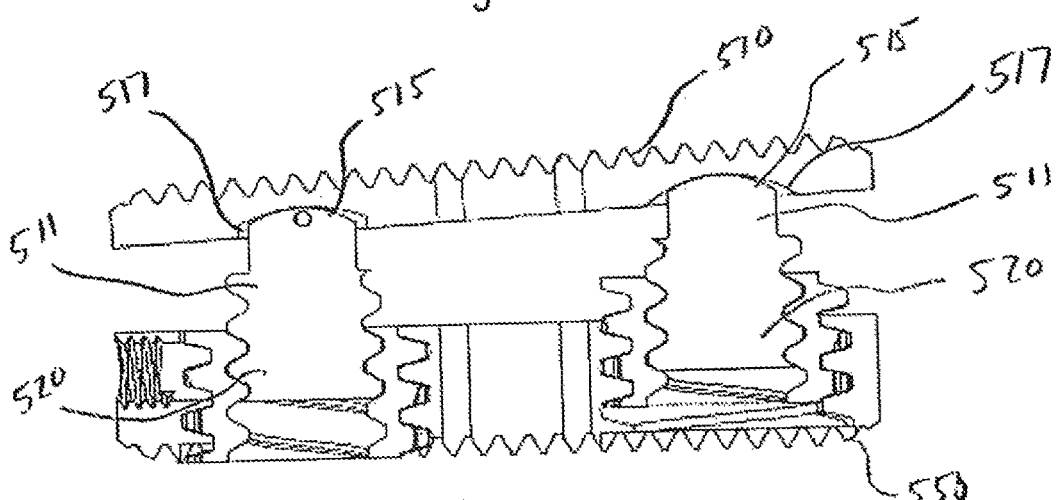
FIG. 10D is a cross-sectional view of the distractible intervertebral body fusion device of FIG. 10A taken along the lines 10D-10D in FIG. 10C.

Referring now to FIGS. 9A-9D, another embodiment of a distractible intervertebral body fusion device 400 includes a single pair of threaded geared posts 423 extending between first member 410 and second member 450 rather than the separate threaded geared sleeves 120, 130 and threaded posts 111,112 described previously. Threaded geared posts 423 each include a threaded geared portion 421 and a post portion 411. Threaded geared portions 421 fit within openings 461 in second member 450 and interface with worm 440 and internal threads 451 to cause the device 400 to distract. Post portions 411 fit within openings 416 in first member 410 and can be attached to washers 418. Washers 418 keep the first member 410 in place relative to the threaded geared posts 423 as the threaded geared posts 423 rotate freely independent of the first member 410 when the device 400 is actuated. Thus, as seen in FIGS. 9C and 9D, the distraction between the first member 410 and the second member 450 is caused by the thicker threaded geared portions 421 while the post portions 411 remain within the openings 416 in first member 410. This leads to a device 400 having increased axial strength.

FIGS. 10A-10D depict a further embodiment of a distractible intervertebral body fusion device 500 that allows for differential adjustment of the threaded geared sleeves 520. Threaded posts 511 can each include an arched portion 515 that corresponds to an arched recess 517 in first member 510. The arched interface between the threaded posts 511 and the first member 510 created by the corresponding arched portions 515 and arched recesses 517 allows the first member 510 to rotate and become angled relative to the second member 550. A pin joint utilizing a pivot pin 572 can be used to keep one interface between the first member 510 and a threaded post 511 stationary, while the other interface is allowed to slide due to the arched surfaces. A placement pin 570 is used to prevent the worm 540 from sliding out of the second member 550 when distracting the device. Worm 540 can be a two-part worm including a first portion 546 having a first threaded section 543 and second portion 548 having a second threaded section 544 that fits onto a post 547 of first portion 546. The two portions 546, 548 can therefore be rotated independently of each other, with each driving a separate threaded geared sleeve 520. Because each threaded geared sleeve 520 can be engaged separately, they can be distracted different amounts, resulting in an angled first member 510 as shown most clearly in FIG. 10D. Such a configuration accommodates lordotic or kyphotic geometry. Optionally, the arched recesses 517 in the first member 550 and arched surfaces 515 of the posts 511 could be replaced with flexural joints or ball or cylinder and socket joints.

Figure 11A:
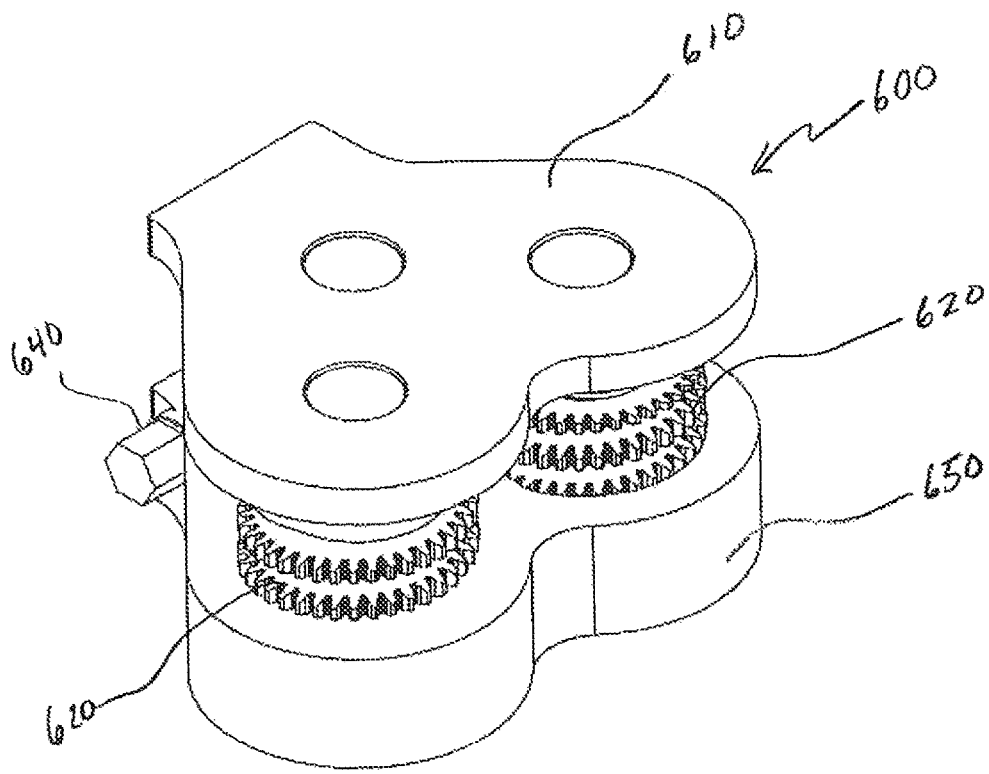
FIG. 11A is a perspective view of a distractible intervertebral body fusion device according to an embodiment of the present invention.
Figure 11B:
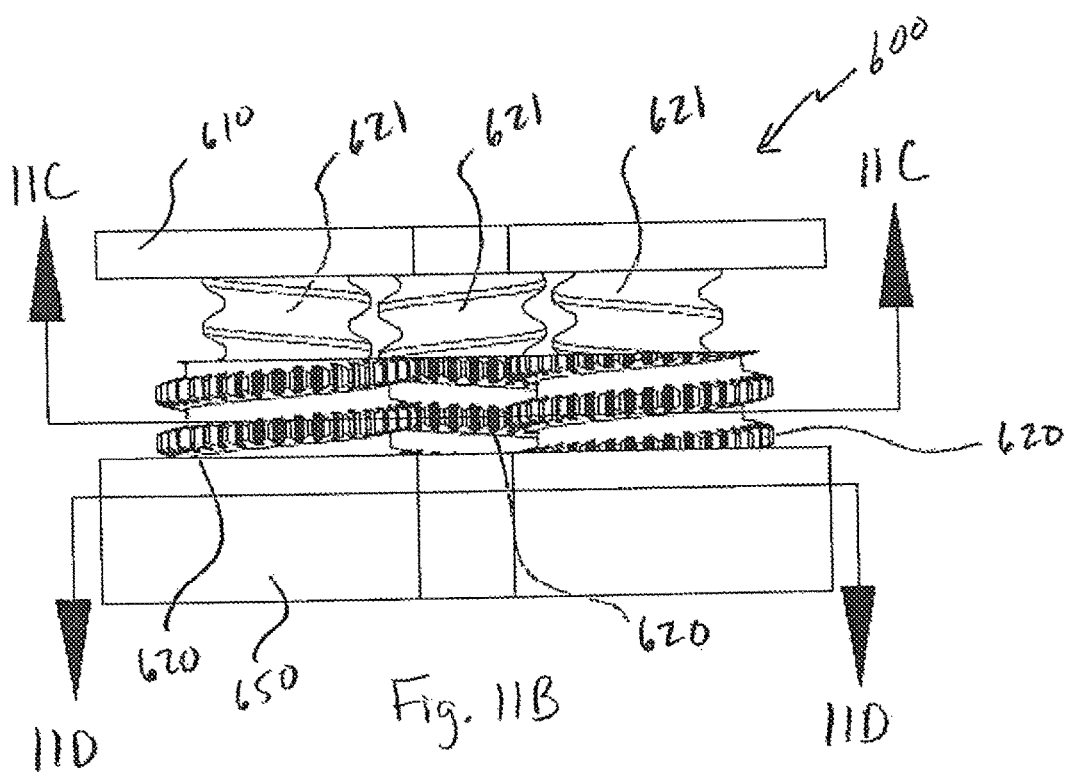
FIG. 11B is a front view of the distractible intervertebral body fusion device of FIG. 11A.
Figure 11C:
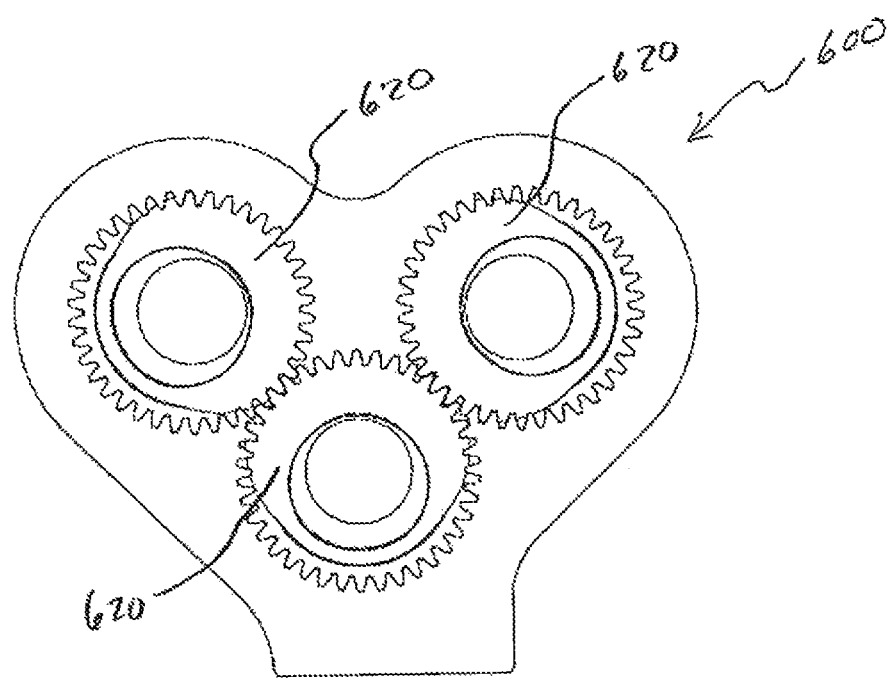
FIG. 11C is a cross-sectional view of the distractible intervertebral body fusion device of FIG. 11A taken along the lines 11C-11C in FIG. 11B.
Figure 11D:
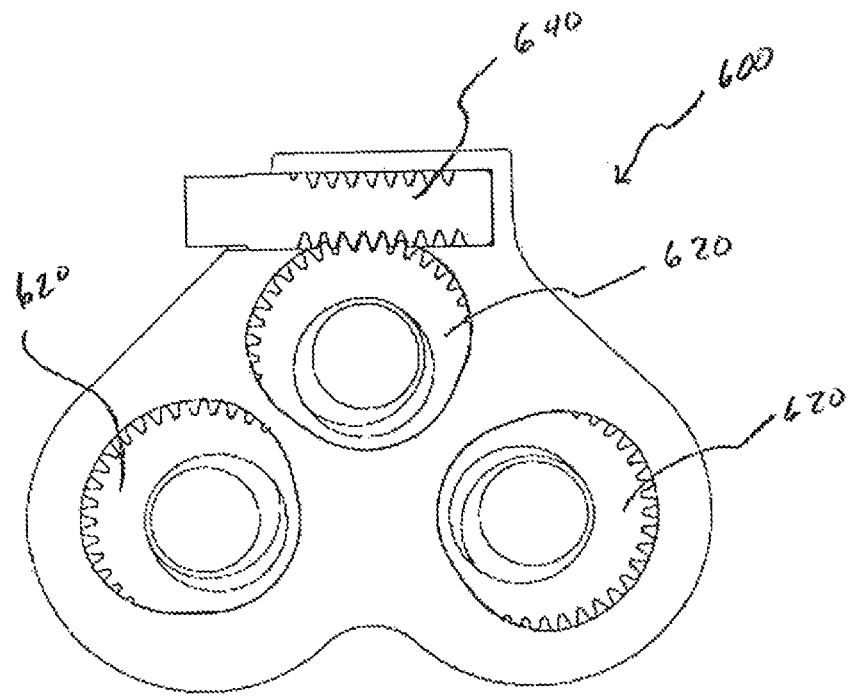
FIG. 11D is a cross-sectional view of the distractible intervertebral body fusion device of FIG. 11A taken along the lines 11D-11D in FIG. 11B.

A distractible intervertebral body fusion device 600 according to another embodiment of the present invention is depicted in FIGS. 11A-11D. Device 600 uses three coaxial screw gear sleeve mechanisms, each having a threaded geared sleeve 620 and a threaded post 621, between first member 610 and second member 650. As seen in FIGS. 11C and 11D, to distract the device, the worm drive 640 is rotated and it engages one of the threaded geared sleeves 620, causing it to rotate. As the first threaded geared sleeve 620 rotates, it engages the other two threaded geared sleeves 620, causing them to rotate and the device 600 to distract. The rotation of the threaded geared sleeves 620 also causes the threaded posts 621 to distract, as described previously. Use of three coaxial screw gear sleeve mechanisms provides for a device having increased strength in the axial direction, a broader surface area for supporting the endplate of the vertebral body, and a more shapely geometry. Optionally, each of the three distraction mechanisms could be actuated independently to adjust the surface of the device in additional degrees of freedom. To achieve some geometries, the drive mechanisms may need to be flexible, in which case a bellows or spiral laser-cut drive mechanism capable of bending and transmitting torque could be implemented. More specifically, one such drive mechanism could wrap around many distraction mechanisms, and distract each one with only one input. In another embodiment, a flexible drive mechanism could be useful in actuating multiple drive mechanisms separately to control the members of the device in many spatial degrees.

Figure 12A:
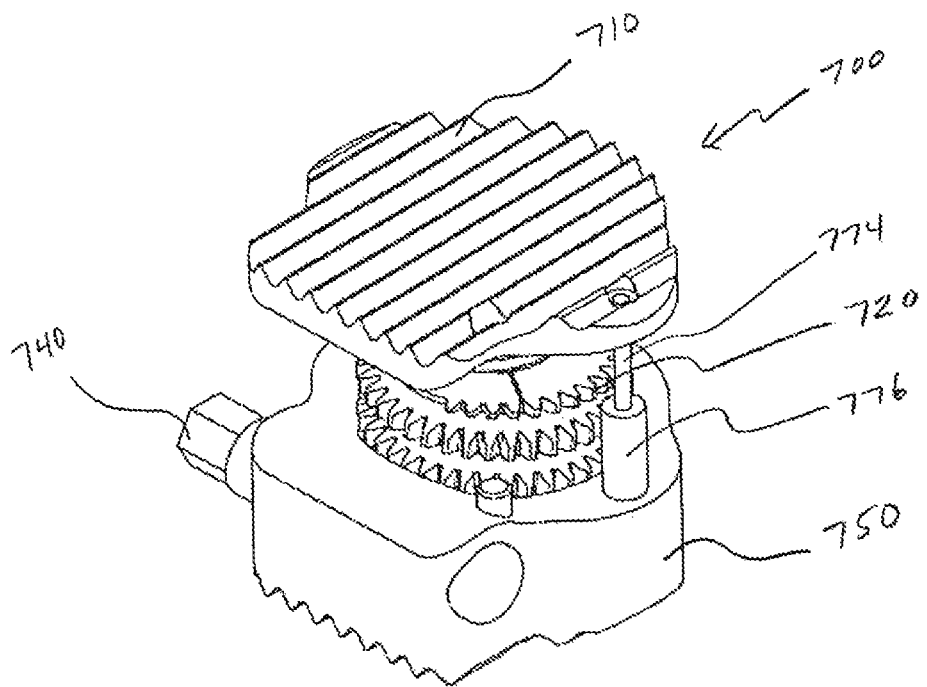
FIG. 12A is a perspective view of a distractible intervertebral body fusion device according to an embodiment of the present invention.
Figure 12B:
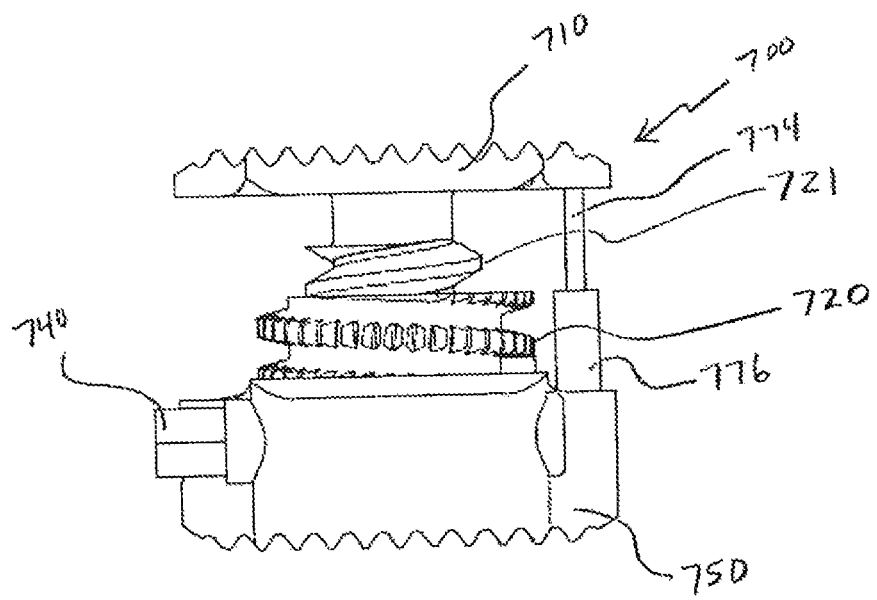
FIG. 12B is a side view of the distractible intervertebral body fusion device of FIG. 12A.
Figure 13A:
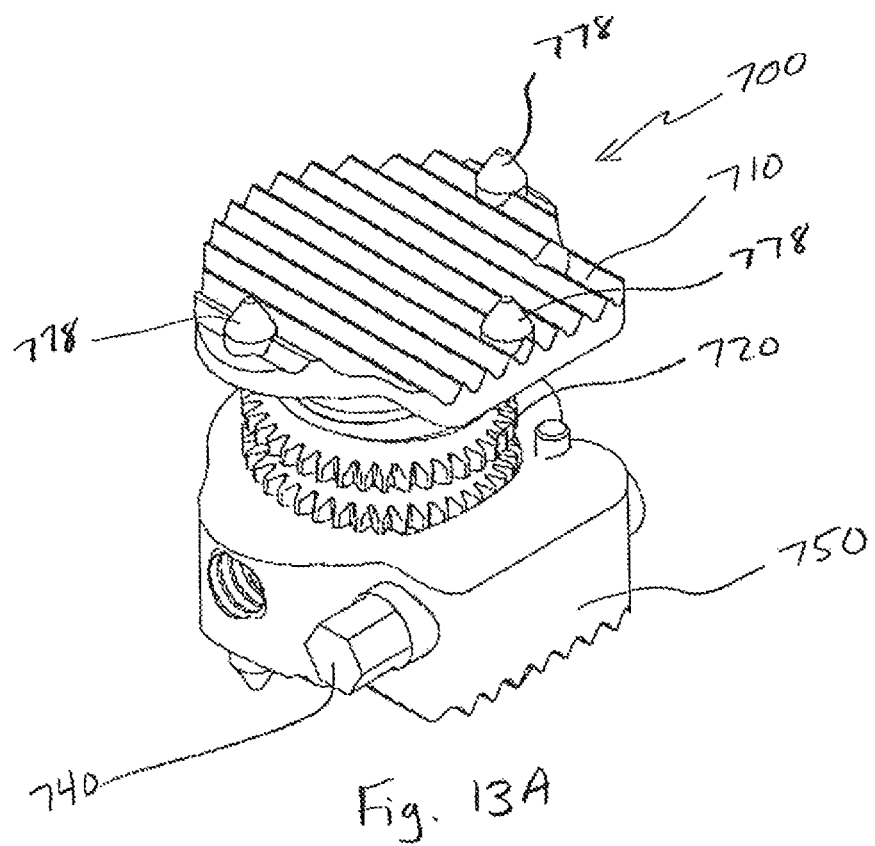
FIG. 13A is a perspective view of a distractible intervertebral body fusion device according to an embodiment of the present invention.
Figure 13B:
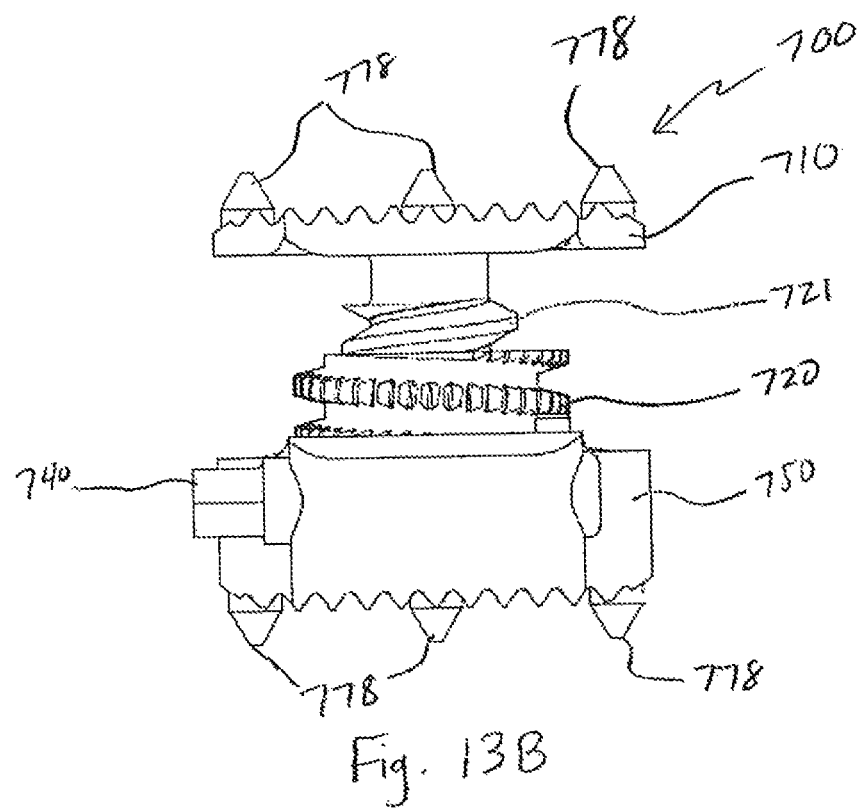
FIG. 13B is a side view of the distractible intervertebral body fusion device of FIG. 13A.
Figure 14A:
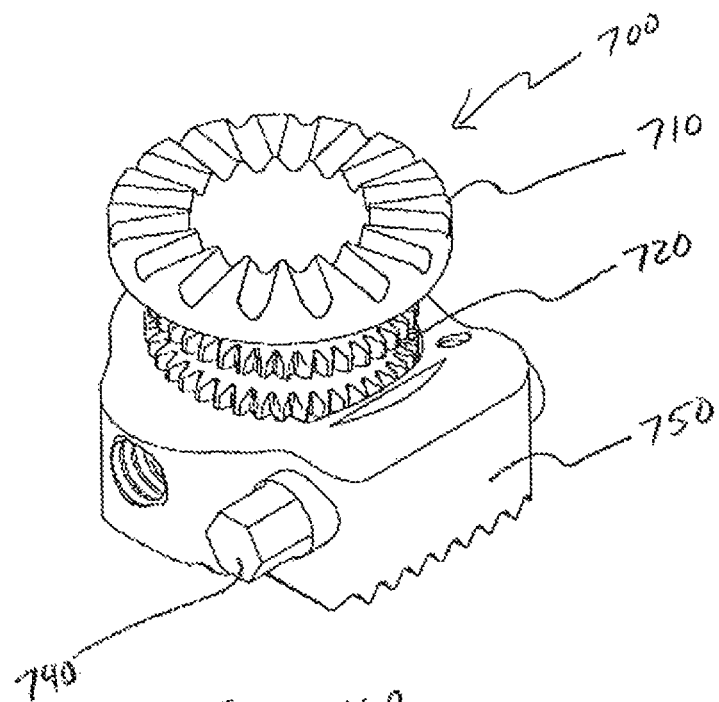
FIG. 14A is a perspective view of a distractible intervertebral body fusion device according to an embodiment of the present invention.
Figure 14B:
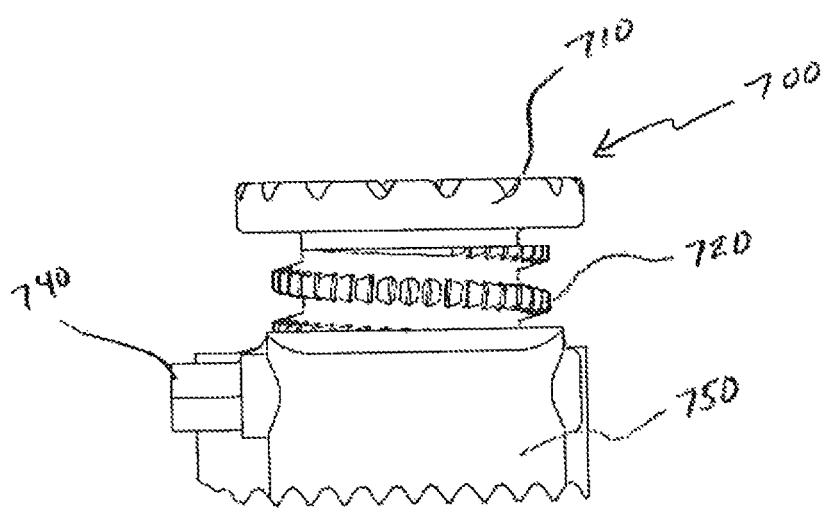
FIG. 14B is a side view of the distractible intervertebral body fusion device of FIG. 14A.

FIGS. 12A and 12B depict a distractible intervertebral body fusion device 700 that employs only a single coaxial screw gear mechanism having a threaded geared sleeve 720 and a threaded post 721 for distracting first member 710 relative to second member 750 with worm 740. Device 700 also can include first 774 and second 776 telescoping support elements. Telescoping support elements 774, 776 serve to maintain the relative rotational positioning of the first member 710 with respect to the second member 750, enabling the threaded geared sleeve 720 to rotate with respect to both the first member 710 and second member 750 to distract the device 700. FIGS. 13A and 13B depict a further variation of device 700 that utilizes a plurality of spikes 778 extending from the first member 710 and second member 750 to rotationally constrain the first member 710 and second member 750. In operation, the spikes 778 contact the adjacent vertebral end plates and fix themselves to the end plates to prevent the first member 710 and second member 750 from rotating relative to each other. A further embodiment is depicted in FIGS. 14A and 14B. This embodiment includes only a threaded geared sleeve 720 between first member 710 and second member 750 and allows the first member 710 to rotate with the sleeve 720 as the device 700 is distracted via rotation of the worm 740. Optionally, first member 710 could be rotationally free with respect to the threaded geared sleeve 720 so that the first member 710 is allowed to engage and not rotate against the endplate of the vertebral body.

In one embodiment, distractible intervertebral body fusion devices as described herein can be made of titanium and the delivery system can be made primarily out of stainless steel. Components of each mechanism that slide against each other can be made of different types of the general material. For example, the first member can be made from Ti 6A1 4V standard titanium, which has high smooth fatigue performance, while the threaded geared sleeves can be made from Ti 6A1 4V ELI, which has high notched fatigue performance Such a combination results in each component being made out of a preferred material for its fatigue notch factor while the overall mechanism implements different materials where components are slidably arranged.

In various embodiments, device is shaped to be ergonomic. Device can have various shapes, such as, for example, rectangular, kidney, or football shaped. A kidney or football shaped device maximizes contact between the device and the vertebral bodies because the end plates of vertebrae tend to be slightly concave. One or both ends of the device may also be tapered in order to facilitate insertion. This minimizes the amount of force needed to initially insert the device and separate the vertebral bodies. In addition, the device may be convex along both its length and its width, or bi-convex. Device can be constructed in various sizes depending on the type of vertebra and size of patient with which it is being used.

Device can be manufactured in various ways with, in some embodiments, different components of the device can be manufactured in different ways. In one embodiment, thread milling can be implemented to manufacture the various threads in device. Wire EDM can be utilized to manufacture some or all of the holes and openings in the device. Assembly jigs and post processing steps can also be utilized to allow the device to be manufactured to exacting standards.

In some embodiments, following distraction of the device, a bone growth stimulant, such as autograft, bone morphogenic protein, or bone enhancing material, may be delivered into device. In one embodiment, bone growth stimulant is delivered through a hollow chamber in insertion tool before insertion tool is disengaged from device. The device supports in-vivo loads during the time fusion occurs between the vertebral bodies.

In one embodiment, the surface of the device can be treated to minimize surface roughness or to reduce pitting of the material within the body. A rough surface or pits can increase the stress on the device, which can result in shortening of the fatigue life and/or reduce fatigue strength. In one embodiment, the surface can be treated with electropolishing, both removing burrs from the edges of the device and finishing the surface. In another embodiment, the surface can be left untreated because a rough surface on the end plates helps prevent accidental extrusion of the device. In one embodiment, the device can also be coated with a highly elastic, impermeable material to extend its fatigue life. Specifically, the impermeable material would prevent the corrosive properties of blood from degrading the device. In another embodiment, the device can be comprised of a biocompatible material, so that no coating is necessary. In a further embodiment, the device can be made of a biodegradable material designed to degrade in the body at a selected stage of the healing process, such as after bone fusion.

In various embodiments, devices as described herein can be used with various bone growth stimulants. In one embodiment, a 3D premineralized silk fibroin protein scaffold carrier can be carried on the surface of or within the device to deliver a bone morphogenetic protein (BMP), which can optionally be combined with modified bone marrow stromal cells (bMSCs) to improve fusion. In other embodiments, a composite chitosan 3D fiber mesh scaffold or a gelatin scaffold can be used. The device can also utilize vascular endothelial growth factor (VEGF) by depositing immobilized VEGF on titanium alloy substrates coated with thin adherent polydopamine film to increase the attachment, viability and proliferation of human dermal cells to promote the development of blood supply to the fused bone through revascularization around the implant. In some embodiments, certain polymers such as biodegradable PLGA could be used to make a scaffold for VEGF to enhance neovascularization and bone regeneration. In some embodiments, VEGF can be used in conjunction with BMPs to inhibit the function of BMPs of promoting osteogenesis to allow the device to be continually adjusted over time. In various embodiments, scaffolds on or around the device could be seeded with bone marrow derived stem cells, dental pulp derived stem cells and adipose derived stem cells. Scaffolds can also be comprised of various materials including polyester (e.g., polylactic acid-co-glycolic acid or poly3-hydroxybuetyrate-co-3-hydorxyvalerate), silk (e.g., biomimetic, apatitie-coated porous biomaterial based on silk fibroin scaffolds), hydrogels such as polycaprolactone, polyepsilon-caprolactone/collagen (mPCL/Col) cospun with PEO or gelatin, mPCL/Col meshes with micron-sized fibers, and mPCL/Col microfibers cosprayed with Heprasil, and porous titanium and titanium alloys (such as a titanium-niobium-zirconium alloy) functionalized by a variety of surface treatments, such as a VEGF or calcium phosphate coating.

In some embodiments, device can include structure adapted to retain bone within an interior of or adjacent to the implant. Such structure can include a micro-level matrix or scaffolding or kerfs, divots, or other similar features in the body of device. Bone may also be retained through use of a porous material such that bone is retained in the interstitial spaces of the material. Larger, extending features may also be implemented. Such features, such as a circumferential shroud, could also have the added function of stiffening the device in torsion.

Figure 15:
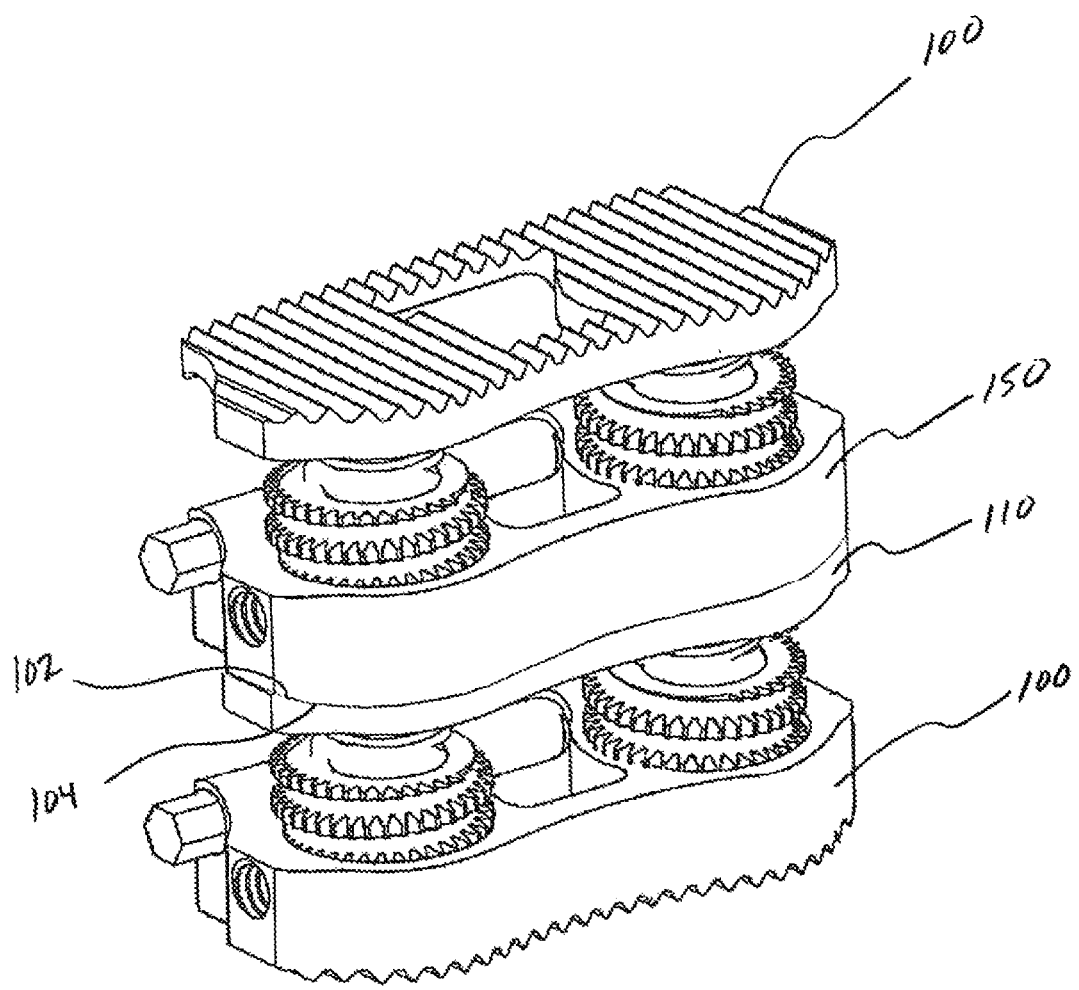
FIG. 15 is a perspective view of a pair of distractible intervertebral body fusion devices according to an embodiment of the present invention.

In some embodiments, more than one distractible intervertebral body fusion device according to the present invention can be implanted into the disc space. As shown in FIG. 15, in one embodiment a pair of devices 100 can be implanted such that the outer surface 104 of the second member 150 of one of the devices 100 directly interfaces with the outer surface 102 of the first member 110 of the other device 100. Such a configuration can allow for use of a smaller access channel for implanting the devices. In one embodiment, the cooperating surfaces 102, 104 of the two devices are flat. Devices 100 can be actuated simultaneously or separately. Devices could also be flipped with respect to each other in order to have both drive mechanisms centrally located. In addition, the devices could be configured to rotate or flex with respect to each other to allow for the bearing surfaces of the devices to adjust their position to comfortably engage with the endplates of the vertebral bodies, or to preserve motion of the spine.

In one embodiment, a rod and screws can be used with the device as part of an assembly affixed to the vertebral body. Specifically, posterior fixation, whereby rod(s) and screws are used to supplement the spine, may be used in combination with the device. In one embodiment, the rod(s) and screws may be affixed to, or designed to engage, the implant. In another embodiment, the members of the device may be extended and, effectively, folded over the sides of the adjacent vertebral bodies so that the device may be affixed to the vertebral bodies with screws placed through the extensions of the members of the device substantially parallel to the plane formed by the endplates of the vertebral bodies. In other embodiments, an adhesive, which may support osteogenesis, may be used to adhere the device to or within the spine.

In another embodiment distractible intervertebral body fusion device can comprise an endplate enhanced with flexures to be capable of tilting front to back and/or side to side. Additionally, coaxial screw gear sleeve mechanisms utilizing at least in part a flexible material can be oriented around the periphery of the device to allow for tilting in a variety of axes. Generally, a device capable of tilting can be beneficial in that providing additional degrees of flexibility built into the device can promote bone growth, distribute stress across the surface of the end plates, and allow the device to adjust to the curvature of an individual's spine.

In one embodiment, the device could be placed within a small sock-like slip made from, for example, silk, which could be filled with bone. As the device expands and the volume of the device increases, the sock would prevent the bone from falling out of the implant and/or allow for more bone to be introduced into the implant from the space around the implant within the sock. Such a sock could be closeable at one end and could attach to the delivery system during implantation of the device. The sock could be released from the delivery system during any of the later steps of implantation.

A device in accordance with the various embodiments can be used for a variety of intervertebral fusion applications, including, for example, cervical, thoracic anterior lumbar, trans-foraminal lumbar, extreme lateral lumbar, and posterior lumbar. Various embodiments of implantation procedures for these applications may be as follows:

Cervical: The device is implanted via an anterior approach at the C3 to C7 levels using autograft. The device is used with supplemental anterior plate fixation.

Trans-foraminal lumbar: The device is implanted via a posterior approach from the L2 to S1 levels using autograft. The device is used with supplemental posterior rod fixation.

Posterior lumbar: The device is implanted via a posterior approach from the L2 to 51 levels using autograft. Two devices are implanted; one on the left side of the disc space and the other on the right side of the disc space. The device is used with supplemental posterior rod fixation.

Anterior lumbar: The device is implanted via an anterior approach from the L3 to S1 levels using autograft. The device is used with supplemental anterior plating fixation of posterior rod fixation.

Extreme lateral lumbar: The device is implanted via a lateral approach from the T12 to L4 levels using autograft. The device is used with supplemental posterior rod fixation.

In another embodiment, the device can be used in vertebral body replacement. After resection of a vertebral body or multiple vertebrae due to fracture or tumor, the device can be distracted to bridge two separate vertebrae. The distracted device bridges and supports the void left after resection. The device can be constructed in different sizes to accommodate the size difference of cervical, thoracic and lumbar vertebrae.

Figure 16A:
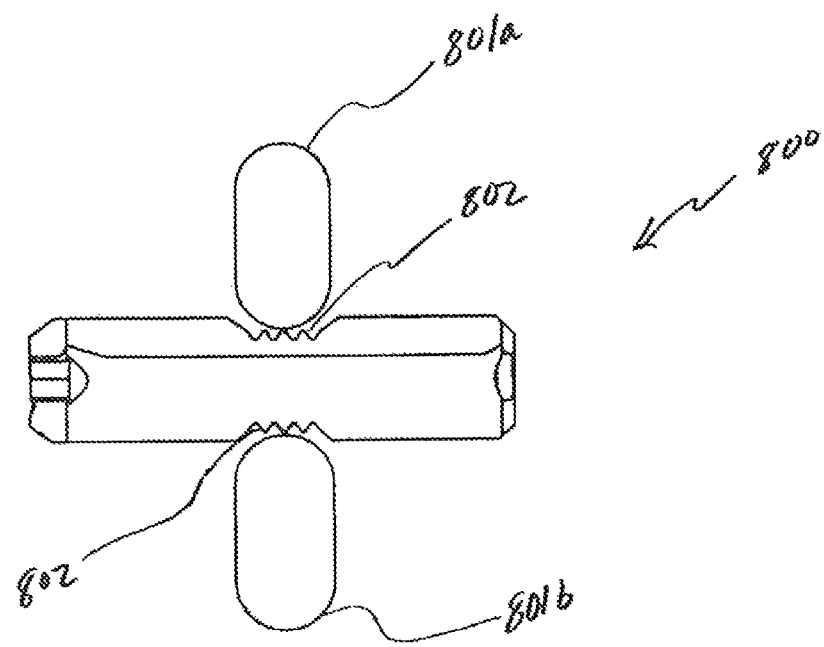
FIG. 16A is a top view of a distractible device according to an embodiment of the present invention in a compressed configuration.
Figure 16B:
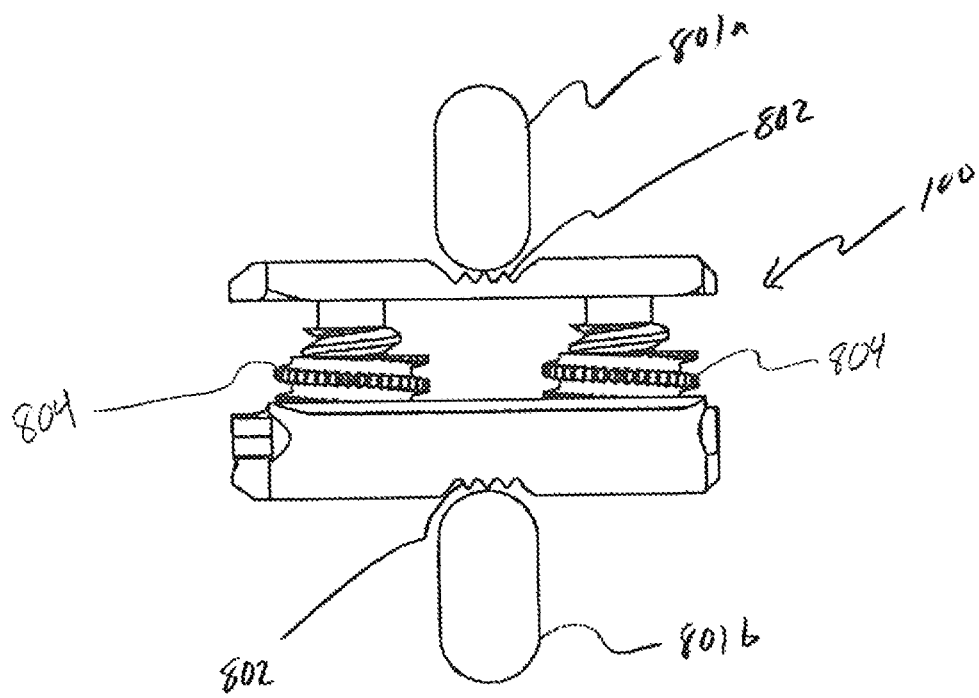
FIG. 16B is a top view of the distractible device of FIG. 16A in an expanded configuration.

In another embodiment, the device can be used as an interspinous distraction device as shown in FIGS. 16A and 16B. The device 800 can be placed between two adjacent spinous processes 801a, 801b through a minimal access system. The device can be inserted in a collapsed configuration to allow ease of placement. Once in position, the device can be actuated to an expanded configuration with coaxial screw gear sleeve mechanisms 804 to lock the vertebrae in a distracted position. Coaxial screw gear sleeve mechanisms 804 can be configured as described previously herein. The device can have gripping teeth 800 at the point of contact with the spinous processes 801a, 801b to help fix it in place.

In another embodiment, the device can be used for interspinous fusion. The device can be placed between two adjacent spinous processes through a minimal access system in a collapsed configuration. Once in position, the device can be actuated to lock the vertebra in a distracted position. The device can have a bolt locking mechanism or similar locking arrangement to lock the device in the distracted position and to lock the locking plates through the spinous processes. The device can also have gripping corrugations or features on the outside to help keep it in place. Autograft or bone fusion enhancing material can be placed in the open space in device.

In another embodiment, the device can be used as a distractible fracture reducing device for osteoporotic bone. The device can be inserted beneath an end plate fracture through a minimally invasive pedicle approach. The device is then actuated with a delivery system actuator. Once the fracture is reduced, the device is explanted and the void is filled with acrylic cement or another bone filler that will strengthen the bone.

In another embodiment, the device can be used in facet joint replacement. After resection of a hypertrophic facet joint, the device can be actuated. Each member can be fixed to adjacent vertebrae with a pedicle screw. This will allow motion similar to that of a facet joint and prevent instability. The device can be part of a soft fusion device system and can be used in combination with an intervertebral disc replacement device. The coaxial screw gear sleeve mechanism or threaded post may also be used to make intervertebral disc replacement devices expandable.

In another embodiment, the device can be used as a programmable distraction cage with a dynameter and bone stimulator. A programmable micro-machine actuator device can be implanted within the device. The device is distracted during implantation and can provide force readings through a radio frequency communicator post-surgery. The shape of the device can be altered while it is implanted by distracting the members with the actuator device, which can result in lordosis, kyphosis, further distraction, or less distraction. In one embodiment, a battery device powers the system and can also form a magnetic field that works as a bone stimulator. The battery life may be limited to a short period of time, such as one week. Small movements of the device can be used to generate electrical energy with piezo-electrics or conducting polymers that may be used to recharge the batteries, capacitors, or other such power storage devices. Alternatively, the device may be powered through an RF inductive or capacitatively coupled arrangement.

In another embodiment, the device can be a self-actuating distractible cage. The device can be inserted into the disc space in a collapsed state. Once the device is released, it can slowly distract to a preset height.

In another embodiment, the device can be used in facial maxillary surgery as a fracture lengthening device for mandibular fractures. The device can be designed with narrow members having perpendicular plates with holes that allow fixation of each member to either a proximal or distal fracture. The device can be actuated to a preset height. This will allow lengthening of the defect in cases of fracture bone loss, dysplasia, or hypoplasia.

In another embodiment, device can be used in orthopedic applications as a lengthening nail for distraction of long bone fractures. After an orthopedic fracture occurs with bone loss, a distractible elongating nail can be placed to lengthen the bone. The elongation occurs over a few days with micrometer movements. This application will involve a distraction device inserted in between the moving portion of the nails exerting counter-distraction forces, which will provide lengthening of the bone.

In another embodiment, the device can be used to replace phalangeal joints in the hand, metatarsal joints in the foot, or calcaneal-talus joints. These joints can have implants that will allow motion of adjacent bones and limit hyper-extension or hyper-flexion.

Figure 17B:
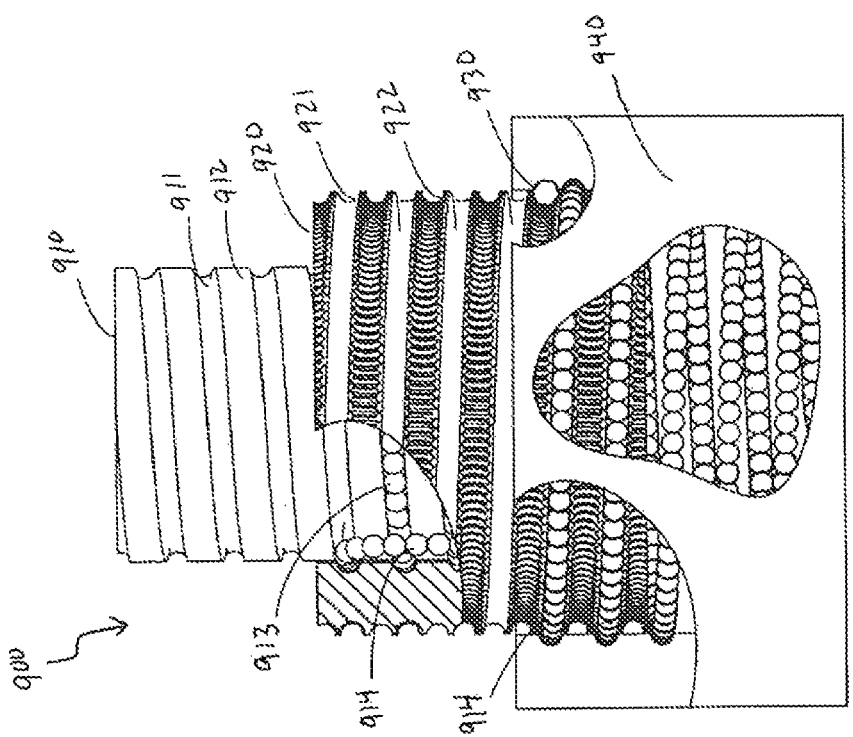
FIG. 17B is a partial cutaway view of the distractible device of FIG. 17A.
Figure 17A:
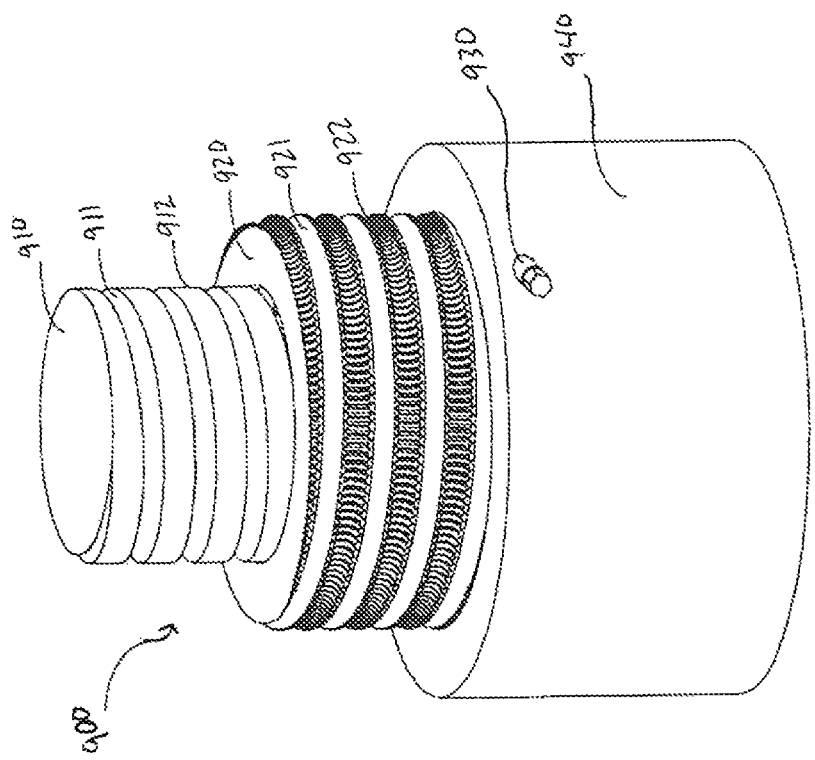
FIG. 17A is perspective view of a distractible device according to an embodiment of the present invention.
Figure 18A:
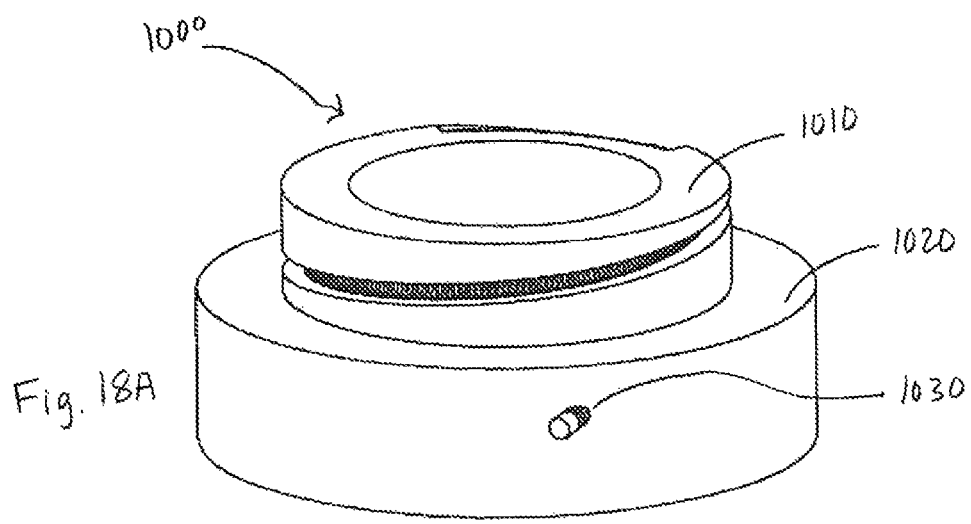
FIG. 18A is a perspective view of a distractible device according to an embodiment of the present invention.
Figure 18B:
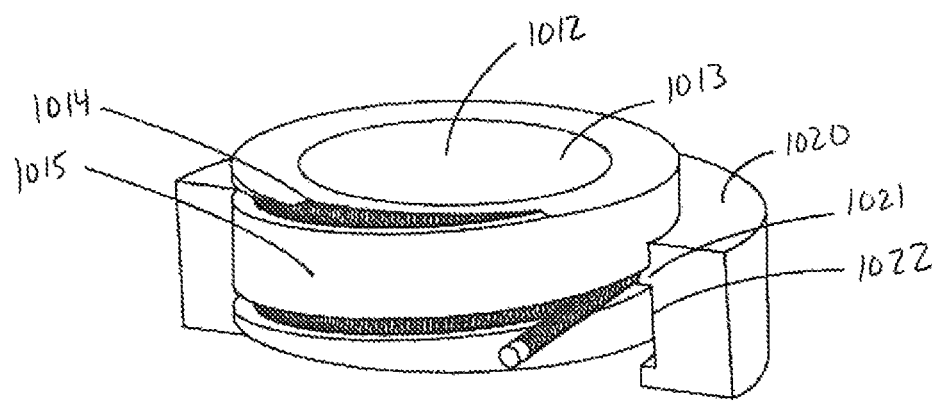
FIG. 18B is a partial view of the distractible device according of FIG. 18A.
Figure 18C:
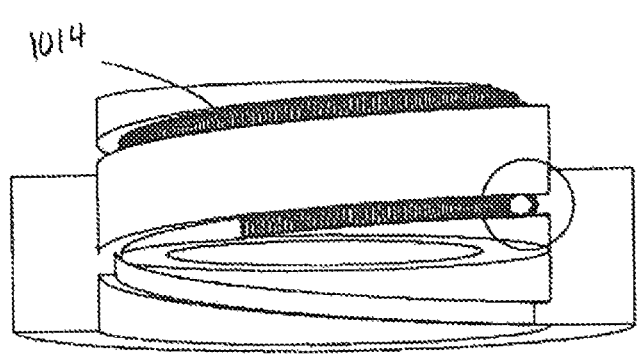
FIG. 18C is a partial view of the distractible device according of FIG. 18A.
Figure 18D:
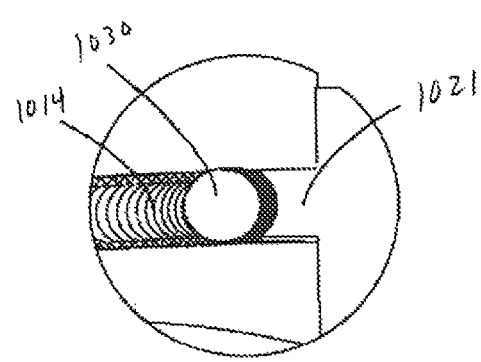
FIG. 18D is a partial view of the distractible device according of FIG. 18A.

FIGS. 17A and 17B depict a distractible device 900 including an enveloping coaxial screw gear sleeve with recirculating bearings according to another embodiment of the present invention. Device 900 includes a post 910, an enveloping coaxial screw gear sleeve 920, a worm 930 and a housing 940. Post 910 includes a smooth outer surface 912 and a machined helical raceway 911 for bearings 913. A helical raceway (not shown) is also machined into inner surface of enveloping coaxial screw gear sleeve 920 that is complementary to helical raceway 911 for accommodating bearings 913. The inner surface of coaxial screw gear sleeve 920 also includes a machined tunnel for recirculation of bearings 913 as the post 910 moves with respect to the sleeve 920. The recirculating bearings are depicted as bearings 914 in FIG. 17B. The outer surface of the enveloping coaxial screw gear sleeve also includes a helical raceway 921 for recirculating bearings 914 and an enveloping screw gear 922. The worm 930 has a helical thread configured to engage the enveloping screw gear 922 of the sleeve 920. The inner surface of the housing 940 has a helical raceway (not shown) that cooperates with helical raceway 921 to retain bearings 914 and a tunnel for recirculating bearings 914 as the coaxial screw gear sleeve 920 moves with respect to the housing 940. Optionally, the coaxial screw gear sleeve 920 could have recirculating bearings both on the inside and the outside of the sleeve and the recirculation tunnel could be between the inside and the outside of the sleeve, facilitating assembly and manufacturing.

To expand the device 900, the worm 930 is rotated clockwise to engage the enveloping screw gear 922 to rotate and translate the enveloping coaxial screw gear sleeve 920 out of the housing 940. This simultaneously causes the post 910 to translate (but not rotate) out of the enveloping coaxial screw gear sleeve 920 and away from the housing 940. Bearings 913, 914 enable the rotation of the enveloping coaxial screw gear sleeve 920 with very little friction, enabling the device 900 to exhibit a very high mechanical advantage and displacement control with very high resolution. The use of the enveloping screw gear 922 enables the interface between the worm 930 and the enveloping coaxial screw gear sleeve 920 to carry substantially higher loading.

Referring now to FIGS. 18A-18D, there can be seen another distractible device 1000 utilizing a coaxial screw gear sleeve according to an embodiment of the present invention. Device 1000 includes an enveloping coaxial screw gear 1010, a housing 1020 and a worm 1030. The outer surface of enveloping coaxial screw gear sleeve 1010 includes a helical groove having a series of enveloping coaxial screw gear teeth 1014. The helical groove can cooperate with an internal thread 1021 on the inner surface 1022 of housing 1020 to allow the device 1000 to carry an axial load. In another embodiment, the gear teeth 1014 can be machined directly into the outer surface of the enveloping coaxial screw gear sleeve 1010. In one embodiment, the outer surface of the enveloping coaxial screw gear sleeve 1010 can be a smooth machined surface that acts like a bearing surface when configured with a similar smooth bearing surface on the inner surface 1022 of housing 1020 to enable the device 1000 to carry a lateral load.

To expand the device 1000, the worm 1030 is rotated to engage the enveloping coaxial screw gear teeth 1014 to rotate and translate the enveloping coaxial screw gear sleeve 1010 with respect to the housing 1020. In one embodiment, the inner surface 1010 and center bore 1012 can be configured to contain a post similar to the post 910 described in FIGS. 17A and 17B to compound the distraction of the device. In one embodiment, no thread 1021 is present on the inner surface 1022 of housing 1020, so the helical groove and/or gear teeth 1014 of the enveloping coxial screw gear sleeve 1010 cause the sleeve 1010 to translate with respect to the housing 1030 as the sleeve 1010 rotates. In such a configuration, the worm 1030 would carry any axial load, unassisted by an inclined interface between the enveloping coaxial screw gear sleeve 1010 and the housing 1020.

Various embodiments of systems, devices and methods have been described herein. These embodiments are given only by way of example and are not intended to limit the scope of the present invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

The invention claimed is:

1. A spinal implant extending along a longitudinal axis between a first region and a second region, the spinal implant comprising:
    an upper body for contacting an upper vertebral body;
    a lower body for contacting a lower vertebral body;
    a first member located in the first region, the first member being translatable in a first direction with respect to cause the upper and lower bodies to move away from one another in at least the first region;
    a second member located in the second region, the second member being translatable in a second direction to cause the upper and lower bodies to move away from one another in at least the second region;
    a first actuator extending along a first axis and operably connected to the first member such that actuation of the first actuator causes the first member to translate in the first direction; and
    a second actuator extending along a second axis and operably connected to the second member such that actuation of the second actuator causes the second member to translate in the second direction;
    wherein the first and second actuators are actuatable independently of one another to independently move the upper and lower bodies away from one another in the respective first and second regions, and wherein the first and second axes of the respective first and second actuators are collinear with one another.

2. The spinal implant of claim 1, wherein the first member is translatable in the first direction with respect to both of the upper and lower bodies, and wherein the second member is translatable in the second direction with respect to both of the upper and lower bodies.

3. The spinal implant of claim 1, further comprising a connector for engaging a delivery system configured to position the spinal implant in an intervertebral space between the upper and lower vertebral bodies, wherein the longitudinal axis extends in a proximal-distal direction and the connector is disposed at a proximal end of the implant, such that the first region is positioned in a proximal portion of the implant and the second region is disposed in a distal portion of the implant.

4. The spinal implant of claim 3, wherein the collinear first and second axes of the respective first and second actuators extend to the proximal end of the implant for actuation by a user.

5. The spinal implant of claim 3, wherein at least a portion of the second actuator extending along the second axis is disposed within a portion of the first actuator extending along the first axis.

6. The spinal implant of claim 1, wherein at least a portion of the second actuator extending along the second axis is disposed within a portion of the first actuator extending along the first axis.

7. The spinal implant of claim 1, wherein the first and second members each include a respective outer surface having external threads thereon.

8. The spinal implant of claim 7, wherein the external threads of the first and second members have gear teeth formed thereon.

9. The spinal implant of claim 7, wherein the external threads of the first and second members engage respective threads formed in the lower body, such that the translation of the first member along the first direction is driven by advancement of the external threads of the first member along the respective threads formed in the lower body, and the translation of the second member along the second direction is driven by advancement of the external threads of the second member along the respective threads formed in the lower body.

10. The spinal implant of claim 1, wherein the first and second actuators are operably connected with gear teeth on the respective first and second members.

11. The spinal implant of claim 1, wherein each of the first and second members includes an opening having internal threads formed therein, wherein the internal threads of the first member are engaged with external threads of a first post member positioned within the opening of the first member, and wherein the internal threads of the second member are engaged with external threads of a second post member positioned within the opening of the second member.

12. The spinal implant of claim 11, wherein the first and second post members are connected to the upper body.

13. The spinal implant of claim 12, wherein the first post member is engaged with the first member such that the first post member telescopes out of the opening of the first member along the first direction while the first actuator causes the first member to translate in the first direction, and wherein the second post member is engaged with the second member such that the second post member telescopes out of the opening of the second member along the second direction while the second actuator causes the second member to translate in the second direction.

14. The spinal implant of claim 1, wherein the first actuator is operably connected to the first member such that actuation of the first actuator causes the first member to rotate about a first axis, and wherein the second actuator is operably connected to the second member such that actuation of the second actuator causes the second member to rotate about a second axis.

15. The spinal implant of claim 14, wherein the first axis extends along the first direction, and the second axis extends along the second direction.

16. The spinal implant of claim 14, wherein the first actuator is a first worm operably connected to an outer surface of the first member, and wherein the second actuator is a second worm operably connected to an outer surface of the second member.

17. The spinal implant of claim 1, wherein each of the first and second members includes an opening having internal threads formed therein, and wherein each of the openings extends entirely through the respective first and second member.

18. The spinal implant of claim 1, wherein each of the first and second members has a respective helical raceway containing recirculating bearings.

19. The spinal implant of claim 1, wherein the first direction of translation of the first member extends along the direction in which the upper and lower bodies move away from one another in the first region, and wherein the second direction of translation of the second member extends along the direction in which the upper and lower bodies move away from one another in the second region.

20. The spinal implant of claim 1, wherein the first and second directions of translation of the respective first and second members extend orthogonal to the collinear first and second axes of the respective first and second actuators.

21. The spinal implant of claim 1, wherein the first member is translatable in the first direction with respect to at least one of the upper and lower bodies, and wherein the second member is translatable in the second direction with respect to at least one of the upper and lower bodies.

22. The spinal implant of claim 1, wherein at least one of the first and second members includes an opening having internal threads formed therein.

* * * * *